US007842513B2

(12) United States Patent
Colgin et al.

(10) Patent No.: US 7,842,513 B2
(45) Date of Patent: Nov. 30, 2010

(54) PREGNANCY DETECTION

(75) Inventors: Mark Colgin, Castle Rock, CO (US); Diane Newman, Castle Rock, CO (US); Cathy Landmann, Highlands Ranch, CO (US); Jay W. Roth, Golden, CO (US); Roger Hurst, Castle Rock, CO (US); Thomas R. Hansen, Fort Collins, CO (US); Kathleen Jeanette Austin, Laramie, WY (US)

(73) Assignees: AspenBio Pharma, Inc., Castle Rock, CO (US); University of Wyoming, Laramie, WY (US)

( * ) Notice: Subject to any disclaimer, the term of this patent is extended or adjusted under 35 U.S.C. 154(b) by 0 days.

(21) Appl. No.: 10/428,244

(22) Filed: May 2, 2003

(65) Prior Publication Data
US 2003/0224452 A1 Dec. 4, 2003

Related U.S. Application Data

(60) Provisional application No. 60/377,987, filed on May 2, 2002, provisional application No. 60/377,166, filed on May 2, 2002, provisional application No. 60/380,043, filed on May 2, 2002, provisional application No. 60/377,921, filed on May 2, 2002, provisional application No. 60/377,165, filed on May 2, 2002, provisional application No. 60/377,355, filed on May 2, 2002, provisional application No. 60/377,829, filed on May 2, 2002, provisional application No. 60/380,042, filed on May 2, 2002.

(51) Int. Cl.
*G01N 33/53* (2006.01)
*G01N 33/543* (2006.01)
*G01N 33/558* (2006.01)

(52) U.S. Cl. .............. 436/510; 435/7.21; 435/7.24; 435/7.8; 435/7.92; 435/7.94; 435/7.95; 435/70.21; 435/331; 435/335; 435/343; 435/287.2; 435/287.7; 435/287.9; 435/806; 436/514; 436/518; 436/530; 436/65; 436/164; 436/807; 436/814; 436/906; 600/551; 600/35

(58) Field of Classification Search ............. 435/6, 435/7.21, 7.8, 7.24, 7.92, 7.94, 7.95, 70.21, 435/331, 335, 343, 806; 436/503, 510, 518, 436/65, 164, 807, 814, 906; 600/551, 35
See application file for complete search history.

(56) References Cited

U.S. PATENT DOCUMENTS

| | | | |
|---|---|---|---|
| 3,689,633 A | 9/1972 | Sanae | |
| 3,817,837 A | 6/1974 | Rubenstein et al. | 162/113 |
| 3,892,855 A | 7/1975 | Short | 424/238 |
| 3,939,350 A | 2/1976 | Kronick et al. | 250/365 |
| 3,996,345 A | 12/1976 | Ullman et al. | 424/12 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,486,530 A | 12/1984 | David et al. | 435/7 |
| 4,554,256 A | 11/1985 | Sasser et al. | 436/510 |
| 4,610,687 A | 9/1986 | Fogwell | 604/891 |
| 4,668,621 A | 5/1987 | Doellgast | 435/13 |
| 4,705,748 A | 11/1987 | Sasser et al. | 435/7 |
| 4,755,460 A | 7/1988 | Bostwick et al. | 435/7 |
| 4,877,742 A | 10/1989 | Maly et al. | 436/65 |

(Continued)

FOREIGN PATENT DOCUMENTS

CA    1185176    4/1985

(Continued)

OTHER PUBLICATIONS

Hicks et al., 2003. Expression of the uterine Mx protein in cyclic and pregnant cows, gilts, and mares. J. Anim. Sci. 81:1552-1561.*

(Continued)

*Primary Examiner*—Mark L Shibuya
*Assistant Examiner*—James L Grun
(74) *Attorney, Agent, or Firm*—Greenlee Sullivan PC

(57) ABSTRACT

This invention provides methods and compositions for testing for pregnancy and non-pregnancy in ungulates and non-hoofed ruminates. The tests provided by this invention are useful during a time that coincides with the estrus cycle during which breeding occurs or the first estrus cycle after breeding of a non-pregnant animal. The tests provided by this invention are useful in estrus and ovulation synchronization programs, with pregnancy testing useful at a time allowing for resynchronization of non-pregnant animals within the first estrus cycle. The tests provided by this invention assay for the presence, absence, or level of a selected IFN-τ-induced protein in a sample from a female animal. The tests of this invention are useful for testing cells, blood, plasma, serum, cells, milk, nasal secretions, ocular secretions, vaginal secretions, urine, and saliva samples. The tests provided by this invention are immunoassays. Polyclonal and monoclonal antibodies useful in such tests, as well as methods of making such antibodies and hybridoma cell lines, are provided. Devices for performing such tests, methods of using such devices, and methods of making such devices are provided. Kits containing such devices are also provided. This invention provides a method for determining readiness for breeding. This invention provides a method for resynchronizing breeding with breeding cycle times of one estrus cycle or shorter. This invention also provides a method for breeding by forcing estrus and artificial insemination by appointment.

22 Claims, 7 Drawing Sheets

U.S. PATENT DOCUMENTS

| | | | | |
|---|---|---|---|---|
| 4,895,804 | A | 1/1990 | Bostwick et al. | 435/240.27 |
| 5,279,942 | A | 1/1994 | Kuniyuki | |
| 5,360,895 | A | 11/1994 | Hainfeld et al. | 530/391.5 |
| 5,418,192 | A | 5/1995 | Borden et al. | 435/69.51 |
| 5,589,457 | A | 12/1996 | Wiltbank et al. | 514/12 |
| 5,622,871 | A | 4/1997 | May et al. | 436/514 |
| 5,646,003 | A | 7/1997 | Barnea et al. | 435/7.24 |
| 5,656,503 | A | 8/1997 | May et al. | 436/514 |
| 5,714,347 | A | 2/1998 | Haas et al. | 435/69.1 |
| 5,739,290 | A | 4/1998 | Horisberger et al. | 530/388.2 |
| 5,869,264 | A | 2/1999 | Horisberger et al. | 435/7.1 |
| 5,919,700 | A | 7/1999 | Borden et al. | 435/372 |
| 5,981,198 | A | 11/1999 | Barnea et al. | 435/7.23 |
| 6,180,102 | B1 | 1/2001 | Hanai et al. | 424/152.1 |
| 6,187,598 | B1 | 2/2001 | May et al. | 436/514 |
| 6,228,660 | B1 | 5/2001 | May et al. | 436/514 |
| 6,352,862 | B1 | 3/2002 | Davis et al. | 436/510 |
| 7,125,728 | B2 * | 10/2006 | Ott | 436/510 |
| 2001/0024799 | A1 | 9/2001 | Jordan et al. | 435/7.9 |
| 2001/0041697 | A1 | 11/2001 | Foster et al. | 514/171 |
| 2002/0192838 | A1 * | 12/2002 | Ott | 436/510 |
| 2003/0059951 | A1 | 3/2003 | Frushour et al. | |
| 2003/0073248 | A1 | 4/2003 | Roth et al. | 436/510 |
| 2003/0143601 | A1 | 7/2003 | Hansen et al. | |
| 2004/0072248 | A1 | 4/2004 | Henderson et al. | |

FOREIGN PATENT DOCUMENTS

| | | |
|---|---|---|
| EP | 0 132 750 | 2/1985 |
| EP | 0 725 081 | 8/1996 |
| WO | WO 88/08534 | 4/1988 |
| WO | WO 94/12537 | 6/1994 |
| WO | WO 99/39208 | 8/1999 |
| WO | WO 99/47934 | 9/1999 |
| WO | WO 00/51520 | 8/2000 |
| WO | WO 00/62075 | 10/2000 |
| WO | WO 02/103352 | 6/2002 |
| WO | WO 03/028582 | 4/2003 |
| WO | WO 2004/095033 | 4/2004 |
| WO | WO 2004/059282 | 7/2004 |

OTHER PUBLICATIONS

Kim et al., 2003. Identification of genes in the ovine endometrium regulated by interferon tau independent of signal transducer and activator of transcription 1. Endocrinol. 144:5203-5214.*

Guo et al., 2002. Induction profile of rat organic anion transporting polypeptide 2 (oatp2) by . . . inducers that activate gene expression through ligand-activated transcription factor pathways. J. Pharmacol. Exp. Therapeutics 300: 206-212.*

Vallejo et al., 2000. Evidence of tissue-specific, post-transcriptional regulation of NRF-2 expression. Biochimie 82: 1129-1133.*

Fu et al., 1996. Translational regulation of human p53 gene expression. EMBO Journal 15: 4392-4401.*

Yokota et al., 1988. Altered expression of the retinoblastoma (RB) gene in small-cell carcinoma of the lung. Oncogene 3: 471-475.*

Talpaz et al., 1992. Interferon-stimulated genes in interferon-sensitive and -resistant chronic myelogenous leukemia patients. Cancer Research 52: 1087-1090.*

Ahrens, P.B. et al "Tumour necrosis factor enhances induction by β-interferon of a ubiquitin cross-reactive protein," (1990) *J. of Gen. Vir.* 71:1675-1682.

Austin, K.J. et al. "Pregnancy-specific protein B induces release of an alpha chemokine in bovine endometrium," (1999) *Endocrinology* 140(1):542-545.

Austin, K.J. et al. "Ubiquitin cross-reactive protein is released by the bovine uterus in response to interferon during early pregnancy," (1996) *Biology of Reproduction* 54:600-660.

Austin, K.J et al. "Complementary deoxyribonucleic acid sequence encoding bovine ubiquitin cross-reactive protein: a comparison with ubiquitin and a 15-kDa ubiquitin homolog," (1996) *Endocrine* 5(2):191-197.

Baboshina, O.V. and Haas, A.L. "Novel multiubiquitin chain linkages catalyzed by the conjugating enzymes $ES_{EPF}$ and RAD6 are recognized by 26 S proteasome subunit 5," (1996) *J. Biol. Chem.* 271:2823-2831.

Bazer, F.W et al. "Interferon tau: a novel pregnancy recognition signal," (1996) *Am. J. Reprod. Immunol.* 37:412-420.

Bazer, F.W. (1995) "Regulation of endometrial responsiveness to estrogen and progesterone by pregnancy recognition signals during the peri-implantation period," In: Dey, S.K. ed., *Molecular and Cellular Aspects of Peri-implantation Processes.* New York, NY, Springer Verlag, pp. 27-47).

Bebington, C. et al. "Ubiquitin cross-reactive protein gene expression is increased in decidualized endometrial stromal cells at the initiation of pregnancy," (1999) *Molecular Human Reproduction* 5(10):966-972.

Bebington, C. et al., "Localization of ubiquitin and ubiquitin-cross-reactive protein in human and baboon endometrium and decidua during the menstrual cycle and early pregnancy," (1999) *Biology of Reproduction* 60:920-928.

Binelli, M. et al., "Interferon-tau modulates phorbol ester-induced production of prostaglandin and expression of cyclooygenase-2 and phospholipase-$A_2$ from bovine endometrial cells," (2000) *Biol. Repro.* 63:417-424.

Binelli M. et al. "Bovine interferon-tau stimulates the Janus kinase-signal transducer and activator of transcription pathway in bovine endometrial epithelial cells," (Feb. 2001) *Biol. Reprod.* 64(2):654-665.

Binelli, M. et al. "Antiluteolytic Strategies to Improve Fertility in Cattle," (Dec. 2001) *Theriogenology* 56(9):1451-1463.

Blomstrom, D.C. et al., "Molecular Characterization of the Interferon-induced 15-kDa Protein," (1986) *J. Biol. Chem.* 261:8811-8816.

Butler, J.E. et al., "Detection and partial characterization of two bovine pregnancy-specific proteins," (1982) *Biol. Reprod.* 26:925-933.

Charleston, B. and Stewart, H.J., "An interferon-induced Mx protein: cDNA sequence and high level expression in the endometrium of pregnant sheep," (1993) *Gene* 137:327-331.

Dailey, R.A. "Synchronization of estrus in dairy heifers and cows," (1984) at http://www.wvu.edu/~exten/infores/pubs/livepoul/dirm8.pdf.

Dixit, V.D. et al. "Pregnancy stimulates secretion of adrenocorticotropin and nitric oxide from peripheral bovine lymphocytes," (Jan. 2001) *Biol. Repro.* 64:242-248.

Drew, M.I. et al., "Pregnancy determination by use of pregnancy-specific protein B radioimmunoassay in llamas," (1995) *JAVMA* 207(2):217-219.

Ellinwood, N.M. et al. "Cloning and characterization of cDNAs for a bovine (*Bos taurus*) Mx protein," (Sep. 1998) *J. Interferon Cytokine Res.* 18(9):745-755.

Farrell, P.J. et al., "Accumulation of an mRNA and protein in interferon-treated Ehrlich ascites tumour cells," (1979) *Nature* 279:523-525.

GenBank Accession #AAC18655 (Jun. 1988) GTP-binding protein (*Bos taurus*).

Haas, A.L. et al., "Interferon induces a 15-kilodalton protein exhibiting marked homology to ubiquitin," (1987) *J. Biol. Chem.* 262(23):11315-11323.

Hansen, T.R. et al. "Transient ubiquitin cross-reactive protein gene expression in the bovine endometrium," (1997) *Endocrinology* 138(11):5079-5082.

Holdsworth, R.J. et al., "A rapid direct radioimmunoassay for the measurement of oestrone sulphate in the milk of dairy cows and its use in pregnancy diagnosis," (1982) *J. Endocrin.* 95:7-12.

Horisberger, M.A. and Hochkeppel, H.K., "An interferon-induced mouse protein involved in the mechanism of resistance to influenza viruses," (1985) *J. Biol. Chem.* 260(3):1730-1733.

Imwalle, D.B. et al., "Effects of melengestrol acetate on onset of puberty, follicular growth, and patterns of luteinizing hormone secretion in beef heifers," (1998) *Biol. Repro.* 58:1432-1436.

Johnson, G.A. et al., "Effects of the estrous cycle, pregnancy, and interferon tau on 2',5'-oligoadenylate synthetase expression in the ovine uterus," (May 2001) *Biology of Reproduction* 64:1392-1399.

Johnson, G.A. et al., "Interferon-tau and progesterone regulate ubiquitin cross-reactive protein expression in the ovine uterus," (2000) *Biology of Reproduction* 62:622-627.

Johnson, G.A. et al,. "Expression of the interferon tau inducible cross-reactive protein in the ovine uterus," (1999) *Biology of Reproduction* 61:312-318.

Johnson, G.A. et al., "Development and characterization of immortalized ovine endometrial cell lines," (1999) *Biol. Repro.* 61:1324-1330.

Johnson, G.A. et al., "Pregnancy and interferon-tau induce conjugation of bovine ubiquitin cross-reactive protein to cytosolic uterine proteins," (1998) *Biology of Reproduction* 58:898-904.

Kiracofe, G.H. et al., "Pregnancy-specific protein B in serum of postpartum beef cows," (1993) *J. Anim. Sci.* 71:2199-2205.

Knight E. Jr. et al., "A 15-kDa itnerferon-induced protein is derived by COOH-terminal processing of a 17-kDa precursor," (1988) *J. Biol. Chem.* 263:4520-4522.

Korant, B.D. et al., "Interferon-induced proteins," (1984) *Journal of Biological Chemistry* 259(23):14835-14839.

Kozbor, D. and Roder, J.C., "The production of monoclonal antibodies from human lymphocytes," (1983) *Immunol. Today* 4(3):72-79.

Loeb, K.R. and Haas, A.L., "The interferon-inducible 15-kDa ubiquitin homolog conjugates to intracellular proteins," (1992) *J. Biol. Chem.* 267(11):7806-7813.

Loeb, K.R. "Conjugates of ubiquitin cross-reactive protein distribute in a cytoskeletal pattern," (1994) *Mol. and Cell. Biol.* 14(12):8408-8419.

Lowe J. et al., "Immunohistochemical localization of ubiquitin cross-reactive protein in human tissues," (1995) *J. Path.* 177:163-169.

Morozumi, T. et al., "Three types of polymorphisms in exon 14 in porcine *Mx1* gene," (Aug. 2001) *Biochem. Genetics* 39(7/8):251-260.

O'Connor, M.L. "Estrous synchronization programs for the dairy herd," (1997) The Pennsylvania State University, College of Agricultural Sciences pp. 1-8.

Ott, T.L. et al., "Effects of the estrous cycle and early pregnancy on uterine expression of mx protein in sheep (*Ovis aries*)," (1998) *Biology of Reproduction* 59:784-794.

Perry, D.J. et al., "Cloning of interferon-stimulated gene 17: the promoter and nuclear proteins that regulate transcription," (1999) *Molecular Endocrinology* 13(7):1197-1206.

Potter, J.L. et al., "Precursor processing of pro-ISG15/UCRP, an interferon-beta-induced ubiquitin-like protein," (1999) *J. Biol. Chem.* 274:25061-25068.

Pru, J.K. et al., "Pregnancy and interferon-τ upregulate gene expression of members of the i-8 family in the bovine uterus," (Nov. 2001) *Biology of Reproduction* 65:1471-1480.

Pru, J.K. "Regulation of bovine uterine proteins and prostaglandin F2a release by interferon-tau," (2000) Ph.D. Thesis, University of Wyoming.

Pru, J.K. et al., "Production, purification, and carboxy-terminal sequencing of bioactive recombinant bovine interferon-stimulated gene product 17," (2000) *Biology of Reproduction* 63:619-628.

Roberts, R.M. "Interferon-tau and pregnancy," (1996) *J. Interferon Ccytokine Res.* 16(4):271-273.

Roberts, R.M. et al., "Maternal recognition of pregnancy," (1996) *Biol. Repro.* 54:294-302.

Rueda, B.R. et al., "Recombinant interferon-τ regulates secretion of two bovine endometrial proteins," (1993)*J. Interferon Res.* 13:303-309.

Sasser, R.G. et al., "Detection of pregnancy by radioimmunoassay of a novel pregnancy-specific protein in serum of cows and a profile of serum concentrations during gestation," (1986) *Biol. Repro.* 35:936-942.

Sasser, R.G. et al., "Detection of early pregnancy in domestic ruminants," (1987) *J. Reprod. Fert., Suppl.* 34:261-271.

Selk, Glenn "Estrus Synchronization of Cattle," Publication F-3163, Oklahoma Cooperative Extension Service, Oklahoma State University (1993) http://www.ansi.okstate.edu/exten/beef/FS-3163.PDF.

Short, E.C. Jr. et al., "Expression of antiviral activity and induction of 2',5'-oligoadenylate synthetase by conceptus secretory proteins enriched in bovine trophoblast protein-1," (1991) *Biol. Repro.* 44:261-268.

Siddoo-Atwal, C. et al., "Elevation of interferon β-inducible proteins in ataxia telangiectasia cells," (1996) *Cancer Research* 56:443-447.

Spencer, T.E. et al., "Expression of interferon regulatory factors one and two in the ovine endometrium: effects of pregnancy and ovine interferon tau," (1998) *Biol. Reprod.* 58:1154-1162.

Spencer, T.E. et al., "Differential effects of intrauterine and subcutaneous administration of recombinant ovine interferon tau on the endometrium of cyclic ewes," (1999) *Biology of Reproduction* 61:464-470.

Sreenan and Diskin, Eds., "The extent and timing of embryonic mortality in the cow," (1986) *Embryonic Mortality in Farm Animals*, Martinus Nijhoff Publishers, pp. 1-11.

Staeheli, P. and Haller, O., "Interferon-induced human protein with homology to protein Mx of Influenza virus-resistant mice," (1985) *Mol. Cell. Biol.* 5(8):2150-2153.

Staeheli, P. et al.,"Polyclonal and monoclonal antibodies to the interferon-inducible protein mx of influenza virus-resistant mice," (1985) *J. of Biol. Chem.* 260(3):1821-1825.

Staggs, K.L. et al., (1998) "Complex induction of bovine uterine proteins by interferon tau," *Biology of Reproduction* 59:293-297.

Stewart. D.M. et al., "Interferon-τ activates multiple signal transducer and activator of transcription proteins and has complex effects on interferon-responsive gene transcription in ovine endometrial epithelial cells," (Jan. 2001) *Endocrinology* 142(1):98-107.

Stewart, H.J. et al., "Trophoblast interferons in early pregnancy of domestic ruminants," (1992) *J. Reprod. Fert. Suppl.* 45:59-68.

Szenci, O. et al., "Comparison of ultrasonography, bovine pregnancy-specific protein b, and bovine pregnancy-associated glycoprotein 1 tests for pregnancy detection in dairy cows," (1998) *Theriogenology* 50:77-88.

Tanaka, K. et al., "The ligation systems for ubiquitin and ubiquitin-like proteins," (1998) *Mol. Cell* 8(5):503-512.

Teixeira, M.G. et al., "Bovine granulocyte chemotactic protein-2 is secreted by the endometrium in response to interferon-tau," (1997) *Endocrine* 6(1):31-37.

Thatcher, W.W. et al.,"Uterine-conceptus interactions and reproductive failure in cattle," (2001) *Theriogenology* 56:1435-1450.

Thatcher, W.W. et al., "Embryo health and mortality in sheep and cattle," (1994) *J. Anim. Sci.* 72(Suppl. 3):16-30.

Thatcher, W.W. et al., "New Strategies to Increase Pregnancy Rates," (2000) www.naab-css.org/education/Thatcher.html.

Towbin H. et al., "A Whole blood immunoassay for the interferon-inducible human Mx protein," (1992) *J. Interferon Res.* 12(2):67-74.

Vallet, J.L. et al.,"A low molecular weight endometrial secretory protein which is increased by ovine trophoblast protein-1 is a β2-microglobulin-like protein," (1991) *J. Endocrinology* 130:R1-R4.

Warnick, L.D. et al.,, "The relationship of the interval from breeding to uterine palpation for pregnancy diagnosis with calving outcomes in holstein cows," (1995) *Theriogenol.* 44:811-825.

Willard, S.T. et al., "Early pregnancy detection and the hormonal characterization of embryonic-fetal mortality in fallow deer," (1998) *Theriogenology* 49:861-869.

Willard, J.M. et al.,"Detection of fetal twins in sheep using a radioimmunoassay for pregnancy -specific protein B," (1995) *J. Anim. Sci.* 73:960-966.

Xiao, C.W. et al.,"Regulation of COX-2 and prostaglandin F synthase gene expression by steroid hormones and Interferon-τ in bovine endometrial cells," (1998) *Endocrinol.* 139:2293-2299.

Yankey, S.J. et al.,"Expression of the antiviral protein Mx in peripheral blood mononuclear cells of pregnant and bred, non-pregnant ewes," (Aug. 2001) *J. of Endocrinology* 170:R7-R11.

Chebel et al., "Effect of resynthconization with GnRH on day 21 after artificial insemination on pregnancy rate and pregnancy loss in lactating dairy cows," *Theriogenology* 2003, 60:1389-1399.

Nighswonger et al., "Rapid communication: The ovine cDNA encoding interferon-stimulated gene product 17 (ISG17)," *J. Animal Sci.* May 2000, 78(5):1393-1394.

Alexander et al. (1998) "HCG Secretion by Peripheral Mononuclear Cells During Pregnancy," *Domestic Animal Endocrinology*, vol. 15(5):377-387.

Walters et al. (2004) *Biochimica et Biophysica Acta*, 1695:73-87.

Zhang et al. (2004) *Journal of Leukocyte Biology*, 75:358-372.

D'Cunha et al. (Jan. 1996) "Immunoregulatory Properties of ISG15, an Interferon-Induced Cytokine," *Proc. Nat. Acad. Sci. USA* 93:211-215.

Roberts et al. (Aug. 1992) "Interferons as Hormones of Pregnancy," *Endocrin. Rev.* 13(3):432-452.

Knight, Jr. E. et al. "IFN-induced 15-kDa protein is released from human lymphocytes and monocytes"; (1991) *J. Immun.* 146(7):2280-2284. (Abstract only).

* cited by examiner

SEQUENCE LISTING

```
<160> NUMBER OF SEQ ID NOS: 6

<210> SEQ ID NO 1
<211> LENGTH: 14
<212> TYPE: PRT
<213> ORGANISM: Bos taurus

<400> SEQUENCE: 1

Gln Arg Leu Ala His Leu Asp Ser Arg Glu Val Leu Gln Glu
1               5                   10

<210> SEQ ID NO 2
<211> LENGTH: 15
<212> TYPE: PRT
<213> ORGANISM: Artificial
<220> FEATURE:
<221> NAME/KEY: MISC_FEATURE
<222> LOCATION: (1)..(15)
<223> OTHER INFORMATION: artificial sequence of SEQ ID NO:1 with a C on
      the n-terminal end

<400> SEQUENCE: 2

Cys Gln Arg Leu Ala His Leu Asp Ser Arg Glu Val Leu Gln Glu
1               5                   10                  15

<210> SEQ ID NO 3
<211> LENGTH: 16
<212> TYPE: PRT
<213> ORGANISM: Bos taurus

<400> SEQUENCE: 3

Thr Val Ala Glu Leu Lys Gln Gln Val Cys Gln Lys Glu Arg Val Gln
1               5                   10                  15

<210> SEQ ID NO 4
<211> LENGTH: 17
<212> TYPE: PRT
<213> ORGANISM: Artificial
<220> FEATURE:
<221> NAME/KEY: MISC_FEATURE
<222> LOCATION: (1)..(17)
<223> OTHER INFORMATION: artificial sequence of SEQ ID NO:3 with a C on
      the n-terminal end

<400> SEQUENCE: 4

Cys Thr Val Ala Glu Leu Lys Gln Gln Val Cys Gln Lys Glu Arg Val
1               5                   10                  15

Gln

<210> SEQ ID NO 5
<211> LENGTH: 16
<212> TYPE: PRT
<213> ORGANISM: Bos taurus

<400> SEQUENCE: 5
```

-continued

```
Trp Leu Ser Phe Glu Gly Arg Pro Met Asp Asp Glu His Pro Leu Glu
1               5                   10                  15

<210> SEQ ID NO 6
<211> LENGTH: 17
<212> TYPE: PRT
<213> ORGANISM: Artificial
<220> FEATURE:
<221> NAME/KEY: MISC_FEATURE
<222> LOCATION: (1)..(17)
<223> OTHER INFORMATION: artificial sequence of SEQ ID NO:5 with a C on
      the n-terminal end

<400> SEQUENCE: 6

Cys Trp Leu Ser Phe Glu Gly Arg Pro Met Asp Asp Glu His Pro Leu
1               5                   10                  15

Glu
```

PREGNANCY DETECTION

CROSS REFERENCE TO RELATED APPLICATIONS

This application claims priority to U.S. Provisional Applications 60/377,987; 60/377,166; 60/380,043; 60/377,921; 60/377,165; 60/377,355; 60/377,829; and 60/380,042, all filed on May 2, 2002, and all of which are incorporated herein by reference to the extent not inconsistent herewith.

FEDERAL FUNDING

This invention was made in part with Government support under NIH/DHHS grant no. R0I HD032475. The Government has certain rights in the invention.

BACKGROUND OF THE INVENTION

Tests for absence of conception, fertilization, pregnancy and non-pregnancy in ungulate, other ruminant animals, and non-ruminant animals, including Artiodactyla, and Perissodactyla, differ in the time after mating/breeding that the tests can be performed, the molecules tested, the analytical methods employed, and the devices or kits used to perform the tests.

Absence of conception has been evaluated in animals, including humans, by measuring immunosuppressive Early Pregnancy Factor (ISEPF or EPF) within 12-48 hours after breeding/mating (U.S. Patent Application No. 2001/0024799 (published Sep. 27, 2001) and WO 99/39208 (published Aug. 5, 1999)). A product for performing such a test is available from Concepto Diagnostics (Knoxville, Tenn.), the ECF™ Dip Stick Test for Cattle. This product is not a test to determine pregnancy.

Fertilization has been evaluated in mammals by measuring Preimplantation Factor (PIF) as early as 4 days after breeding (U.S. Pat. Nos. 5,646,003 (issued Jul. 8, 1997) and 5,981,198 (issued Nov. 9, 1999). PIF has also been measured to test for pregnancy. PIF is not measured by immunoassay.

Pregnancy has been evaluated by a variety of methods. Bovine Antigen Glycoprotein (U.S. Pat. Nos. 4,755,460 (issued Jul. 5, 1988) and 4,895,804 (issued Jan. 23, 1990)) can be measured about 12-15 days after breeding. Early Pregnancy Factor (EPF) (U.S. Pat. No. 4,877,742 (issued Oct. 31, 1989) and WO 00/51520 (published Sep. 8, 2000) levels can be measured at about 20-40 days after breeding, such as with KEMS BioTest Ltd. (Littleton, Colo.) Animal Rapid Test for Bovine Pregnancy. Progesterone levels can be measured in milk or blood samples collected after 22-24 days, such as offered at Rocky Mountain Instrumental Laboratories Inc. (Fort Collins, Colo.), but measurements of progesterone in milk at days 18-22 yield unacceptably high rates of false positives (Oltenacu et al. (1990) J. Dairy Sci. 73:2826-2831 and Markusfeld et al. (1990) Br. Vet. J. 146:504-508). Pregnancy-Specific Protein B (PSPB; U.S. Pat. Nos. 4,554,256 (issued Nov. 19, 1985); 4,705,748 (issued Nov. 10, 1987); European Patent No. 0132750 (published Feb. 13, 1985); and Sasser, R. G. et al. (1986) "Detection of pregnancy by radio-immunoassay of a novel pregnancy-specific protein in serum of cows and a profile of serum concentrations during gestation" Biol. Repro. 35:936-942) can be tested about 24-25 days after breeding. PSPB has also been tested in llamas (Drew, M. I. et al. (1995) "Pregnancy determination by use of pregnancy-specific protein B radioimmunoassay in llamas" JAVMA 207(2):217-219); deer (Willard, S. T. et al. (1998) "Early pregnancy detection and the hormonal characterization of embryonic-fetal mortality in fallow deer" Theriogenology 49:861-869); and sheep (Willard, J. M. et al. (1995) "Detection of fetal twins in sheep using a radioimmunoassay for PSPB" J. Anim. Sci. 73:960-966) for detection of twins. PSPB tests have been problematic because PSPB is detectable after calving (Kiracofe, G. H. et al. (1993) "PSPB in serum of postpartum beef cows" J. Anim. Sci. 71:2199-2205). Ultrasound can be performed after about 28 days. Palpation to determine pregnancy on cows can be performed on cows after about 35 days. Estrone sulfate analysis in urine or serum after Day 100 confirms pregnancy in cows (Holdsworth et al. (1982) J. Endocrin. 95:7-12 and Warnick et al. (1995) Theriogenol. 44:811-825). Pregnancy Associated Glycoproteins (PAGs) can also be detected during early pregnancy (WO 99/47934 [published Sep. 23, 1999]). Szenci, O. et al. (1998) "Comparison of Ultrasonography, Bovine Pregnancy-Specific Protein B, and Bovine Pregnancy-Associated Glycoprotein 1 Tests for Pregnancy Detection in Dairy Cows" Theriogenology 50:77-88, describes a comparison of bovine pregnancy tests for days 26 to 58 after artificial insemination (AI).

All above-mentioned pregnancy tests that can be performed during the first estrus cycle have not been reported as performed on serum samples. None of these tests involve assaying proteins known to be induced by interferon-tau (IFN-τ).

IFN-τ is a protein secreted by the conceptus that is involved in the maternal recognition of pregnancy in many mammals (Stewart, H. J. et al. (1992) "Trophoblast interferons in early pregnancy of domestic ruminants" J. Reprod. Fert. Suppl. 45:59-68; Roberts, R. M. et al. "Maternal Recognition of Pregnancy" (1996) Biol. Repro. 54(2):294-302; and Roberts, R. M. "Interferon-tau and pregnancy" (1996) 16(4):271-3). In ungulates, the conceptus must signal its presence to the maternal system to alter the uterine-dependent ovarian cycle. This is accomplished by production and secretion of IFN-τ by the trophectoderm of the conceptus (Bazer, F. W et al. (1996) "Interferon tau: a novel pregnancy recognition signal" Am. J. Reprod. Immunol. 37:412-420). IFN-τ promotes maintenance of pregnancy by altering endometrial gene expression and blocking the uterine luteolytic signal (Bazer, F. W. (1995) "Regulation of endometrial responsiveness to estrogen and progesterone by pregnancy recognition signals during the peri-implantation period" In: Dey, S. K. ed., Molecular and Cellular Aspects of Peri-implantation Processes. New York, N.Y., Springer Verlag, pp. 27-47). IFN-τ is produced by the trophoblast between Days 11 and 21 of pregnancy in sheep and between Days 12 and 26 of pregnancy in cattle. The critical period during which pregnancy is maintained or fails in cattle occurs between Days 15 and 17 (Binelli, M (2001) "Antiluteolytic Strategies to Improve Fertility in Cattle" Theriogenology 56(9):1451-1463).

In cows, the estrus cycle is about 21 days. To determine when a cycling cow is ready for breeding, the cow can be observed for behavioral estrus. Alternatively, a cow can be induced or forced into estrus with effective hormone therapies. Estrus of an entire herd can be synchronized (U.S. Pat. Nos. 3,892,855 issued Jul. 1, 1975, and 4,610,687 issued Sep. 9, 1986). Estrus synchronization, or preferably ovulation synchronization, is used in timed AI (TAI) breeding programs. TAI breeding programs involve precise estrus synchronization which allows for timed breeding without monitoring for behavioral estrus. Examples of methods for forcing estrus include U.S. Pat. No. 5,589,457 (issued Dec. 31, 1996), Ovsynch (Pharmacia Animal Health, Peapack, N.J.), Cosynch, Select Synch, Modified Select Synch, MGA/PGF, and Syncro-Mate-B. Such methods typically employ hormones such as prostaglandins, e.g. PGF$_{2\alpha}$ (Lutalyse®, Pharmacia Upjohn, Peapack, N.J.; Bovilene®, Syntex; Animal Health, Des Moines, Iowa; and Estrumate® Haver Lockhart, Shawnee, Kans.), and gonadotropin releasing hormone (GnRH). Ovsynch involves a GnRH injection followed by a prostaglandin injection one week later, followed by a second GnRH injection 48 hours later. Insemination is ideally then performed at about 12-18 hours, or about 16 hours, after the second GnRH injection. Ovsynch is maximally effective when implemented between Days 18-20 of a 20-day bovine estrus cycle (Thatcher, W. W. et al. (2000) "New Strategies to Increase Pregnancy Rates," a website publication of Presynch (Pharmacia Animal Health, Peapack, N.J.) can be used to synchronize heifers before implementing Ovsynch. Presynch involves two prostaglandin injections. Some of the above-mentioned methods are also used on non-cycling cows to induce cycling, such as in lactating dairy cows. After precise estrus synchronization, animals need not be monitored for behavioral estrus and may be bred by appointment. Some animals may need estrus presynchronization before estrus synchronization. Melengestrol acetate (MGA™) in feed (Imwalle, D. B. et al. (1998) "Effects of melengestrol acetate on onset of puberty, follicular growth, and patterns of luteinizing hormone secretion in beef heifers" Biol. Repro. 58:1432-1436) or implants (U.S. Patent Publication No. 2001/0041697, published Nov. 15, 2001) can be used for presynchronizing estrus in heifers. Resynch is a program whereby animals are synchronized and bred, and then those animals that are determined to be, open (not pregnant) are again synchronized and rebred.

Prostaglandin alone has been administered sequentially or simultaneously with artificial insemination to reduce the number of insemination administrations per herd required for achieving pregnancy (WO 02/04006, published Jan. 17, 2002).

Prostaglandin can be used as a single injection. An injection of about 2-5 cc of Lutalyse (prostaglandin PGF$_2\alpha$) will induce an animal with a mature corpus luteum to come into estrus in about 48-96 hours. Cattle typically have a functional corpus luteum during Days 5-18 of the cycle (Estrus Synchronization of Cattle, Publication F-3163, Oklahoma Cooperative Extension Service, Oklahoma State University). Animals induced into estrus can be bred at 2-5 days following a prostaglandin injection. Single injection prostaglandin programs are often used with estrus synchronization, corpus luteum palpation, or behavioral heat detection because only animals in certain stages of the estrus cycle will respond by going into estrus. Breeding by appointment with a standard prostaglandin program has not been recommended because the interval from injection to estrus varies depending on the stage of the cycle when prostaglandin is administered. For example, if a cow is at cycle Day 7-8 or Day 15-17, timed AI can be performed at about 72-80 hours after the injection. A risk of using prostaglandin injection for forcing estrus is that prostaglandin can cause abortion when given to pregnant animals. Estrus and ovulation synchronization allows cattle managers to concentrate heat detection efforts in a relatively short period of time or allows for TAI, which requires no heat detection.

There is a need in the art to determine pregnancy status during the breeding of livestock. In cattle, conception rates are low (Streenan and Diskin, Eds. (1986) *Embryonic Mortality in Farm Animals*, Martinus Nijhoff Publishers, 1-11) and spontaneous abortion rates are high, making pregnancy/non-pregnancy determination and rebreeding/inseminating important management tools. Particularly there is a need to determine pregnancy/non-pregnancy status during the estrus cycle in which insemination occurs or the first estrus cycle after insemination so that animals that are not pregnant can be most economically rebred. This need is particularly strong when raising livestock such as cattle, especially on dairy farms.

There is a need in the art for tests that determine pregnancy, and particularly non-pregnancy, status of animals during the estrus cycle in which insemination occurs or during the first estrus cycle after insemination. Knowing which animals are non-pregnant allows efforts to be directed towards forcing non-pregnant animals into estrus and/or watching for signs of estrus, in preparation for insemination, to decrease the time an animal is not pregnant. Pregnancy is dependent, not only on conception/fertilization but also on maternal recognition of pregnancy during the critical period, which allows for implantation. Up to 40% of total embryonic losses are estimated to occur between Days 8 and 17 of pregnancy in cattle (Thatcher, W. W. et al. (1994) "Embryo Health and Mortality in Sheep and Cattle" J. Anim. Sci. 72(Suppl. 3):16-30). In the absence of reliable pregnancy tests, the earliest time at which a non-pregnant animal can be identified is at the beginning of a new estrus cycle, by observation of behavioral estrus. Optimally, pregnancy/nonpregnancy status is determined towards the end of or after the critical period when pregnancy is maintained, Days 15-17, according to Binelli, M. et al. (2001) "Antiluteolytic Strategies to Improve Fertility in Cattle" Theriogenology 56:1451-1463, but before the end of the first estrus cycle, Days 18-20, allowing timed artificial insemination programs to be maximally effective. This reference discloses that pregnancy/non-pregnancy status is optimally determined during Days 17-18.

Proteins that are induced by IFN-τ include GCP-2 (WO 94/12537 (published Jun. 9 1994) and Staggs, K. L. et al. (1998) "Complex Induction of Bovine Uterine Proteins by Interferon Tau" Biology of Reproduction 59:293-297), 2',5'-oligoadenylate synthetase (Short, E. C. et al. (2001) "Expression of antiviral activity and induction of 2',5'-oligoadenylate synthetase by conceptus secretory proteins enriched in bovine trophoblast protein-1" Biol. Repro. 44:261-268), β2-microglobulin (Vallet, J. L. et al. (1991) "A low molecular weight endometrial secretory protein which is increased by ovine trophoblast protein-1 is a β2-microglobulin-like protein" J. Endocrinology 130:R1-R4), IFN regulatory factors 1(IRF-1) and 2 (IRF-2) (Spencer, et al. (1998) Biol. Reprod. 58:1154-1162; and Binelli M. et al. (2001) Biol. Reprod. 64(2):654-665), GCP-2 (Teixeira, M. G. et al. (1997) Endocrine 6:31-37); and 1-8U, 1-8D, and Leu-13/9-27 (Pru, J. K. et al. (2001) "Pregnancy and Interferon-τ Upregulate Gene Expression of Members of the I-8 Family in the Bovine Uterus" Biology of Reproduction 65:1471-1480, and Pru, J. K. (2000) "Regulation of bovine uterine proteins and prostaglandin F2a release by interferon-tau" Ph.D. Thesis, University of Wyoming). Leu-13 is the name of the protein encoded by the 9-27 gene. Cyclooxygenase-2 (COX-2) (Xiao, C W et al. (1998) "Regulation of COX-2 and prostaglandin F2α synthase gene expression by steroid hormones and IFN-τ in bovine endometrial cells" Endocrinol. 139: 2293-2299 and Thatcher, W. W. et al. (2001) "Uterine-conceptus Interactions and Reproductive Failure in Cattle" Theriogenology 56:1435-1450) and PLA$_2$ (Binelli, M. et al. (2000) "Interferon-tau modulates phorbol ester-induced production of prostaglandin and expression of cyclooygenase-2 and phospholipase-A$_2$ from bovine endometrial cells" Biol. Repro. 63:417-424) are also regulated by IFN-τ.

Teixeira, M. G. et al. (1997) "Bovine Granulocyte Chemotactic Protein-2 is Secreted by the Endometrium in Response to Interferon-tau" Endocrine 6(1):31-37 report that bovine 1-8 transcripts were detected on Days 15 and 18 of pregnancy and were absent on Day 12 of pregnancy and during the estrus cycle. Bovine 1-8 gene family members are not known to be secreted. This reference also reported that polyclonal antibodies to a GCP-2 peptide were generated in sheep, and used to demonstrate that GCP-2 is secreted by cultured endometrial cells, representing Day 14 of the estrus cycle, when dosed with IFN-τ.

Mx encodes a monomeric GTPase and is induced by IFN-τ (Ott, T. L. et al. (1998) "Effects of the Estrous Cycle and Early Pregnancy on Uterine Expression of Mx Protein in Sheep (*Ovis aries*)" Biology of Reproduction 59:784-794). In Ott et al. (1998), ovine Mx protein was detected using a monoclonal antibody directed against the amino terminus of human MxA (1319.35.126, supplied by M. Horisberger, Novartis, Basel Switzerland) and a Super ABC Mouse/Rat Kit (Biomeda, Foster City Calif.). U.S. Patent Application No. 60/299,553 describes a method of determining pregnancy status of an animal by assaying the level of Mx and comparing it to the level of Mx in a non-pregnant animal. Mx protein was detected with ovine Mx peptide antiserum (#90618-2). Yankey, S. J. et al. (2001) "Expression of the antiviral protein Mx in peripheral blood mononuclear cells of pregnant and bred, non-pregnant ewes" J. of Endocrinology 170:R7-R11, describes the presence of Mx in peripheral blood mononuclear cells of pregnant ewes at Day 15 of pregnancy. Mx protein can also be used to detect viral infection (EP 0 725 081, published Aug. 7, 1996) using monoclonal antibodies to human Mx. Antibodies to human Mx and immunoassays for Mx have been described (Staeheli, P. and Haller, O. (1985) "Interferon-induced human protein with homology to protein Mx of Influenza virus-resistant mice" Mol. Cell. Biol. 5(8): 2150-2153; Towbin H. et al. (1992) "A Whole Blood Immunoassay for the Interferon-Inducible Human Mx Protein" J. Interferon Res. 12(2):67-74; U.S. Pat. Nos. 5,869,264 (issued Feb. 9, 1999); 5,739,290 (issued Apr. 14, 1998); and 6,180,102 (issued Jan. 30, 2001). Antibodies to mouse Mx are described in Staeheli, P. et al. (1985) Mol. Cell Biol. 5:2150-2153; Staeheli, P. et al. (1985) J. Biol. Chem. 260(3):1821-1825; and Horisberger, M. A. et al. (1985) J. Biol. Chem. 260(3):1730-1733. One of the monoclonal antibodies in Towbin (1992) is reported to react with other species Mx proteins (mouse, rat, bovine, and porcine), in addition to human Mx.

Another IFN-τ-induced protein is ubiquitin cross-reactive protein (UCRP), which was first identified in humans (Farrell, P. J. et al. (1979) Nature 279:523-525) and later characterized (Koran, B. D. (1984) "Interferon-induced Proteins" Journal of Biological Chemistry 259(23):14835-14839; Blomstrom, D. C. et al. (1986) J. Biol. Chem. 261:8811-8816; and Knight E. Jr. et al. (1988) J. Biol. Chem. 263:4520-4522). Human UCRP (hUCRP) and mouse UCRP encode proteins that are processed to 17 kDa but that migrate as 15 kDa on PAGE) gels (Potter, J. L. et al. (1999) "Precursor processing of pro-ISG15/UCRP, an interferon-beta-induced ubiquitin-like protein" J. Biol. Chem. 274:25061-25068) are similar to ubiquitin, and are upregulated by interferon (IFN), hence they are also known as interferon-stimulated gene 15 (ISG15). ISG15 is involved in the viral response and in the recognition of pregnancy (Bebington, C. et al. (1999) "Localization of Ubiquitin and Ubiquitin Cross-Reactive Protein in Human and Baboon Endometrium and Decidua During the Menstrual Cycle and Early Pregnancy" Biology of Reproduction 60:920-928 and Bebington, C. et al. (1999) "Ubiquitin Cross-Reactive Protein Gene Expression is Increased in Decidualized Endometrial Stromal Cells at the Initiation of Pregnancy" Molecular Human Reproduction 5(10):966-972). Like ubiquitin, ISG15 becomes covalently attached to targeted intracellular proteins via a C-terminal LRGG amino acid sequence. Proteins that are coupled to ubiquitin often are degraded through the 26 S proteasome (Baboshina O V (1996) "Novel multiubiquitin chain linkages catalyzed by the conjugating enzymes ESEPF and RAD6 are recognized by 26 S proteasome subunit 5" J. Biol. Chem. 271:2823-2831). Ubiquitin is conjugated to other proteins by E2-conjugating enzymes (Tanaka, K. et al. (1998) "The ligation systems for ubiquitin and ubiquitin-like proteins" Mol. Cell 8:503-512).

The 17 kDa bovine analog of hUCRP (ISG15) was identified as bovine UCRP (bUCRP) or ISG17 (Austin, K. J. et al. (1996) "Ubiquitin Cross-Reactive Protein is Released by the Bovine Uterus in Response to Interferon During Early Pregnancy" Biology of Reproduction 54:600-606; Austin, K. J et al. (1996) "Complementary Deoxyribonucleic Acid Sequence Encoding bovine Ubiquitin Cross-Reactive Protein" Endocrine 5(2):191-197; and Perry, D. J. et al. (1999) "Cloning of Interferon-Stimulated Gene 17: The Promoter and Nuclear Proteins That Regulate Transcription" Molecular Endocrinology 13:1197-1206). ISG17 becomes covalently linked to targeted intracellular proteins, is released from endometrial cells, and may function as a paracrine modulator. Unlike ISG15, ISG17-conjugated proteins continue to accumulate rather than be degraded. Two of the 1-8 gene family members, bovine 1-8U and bovine Leu-13, have high homology with the E2-conjugating enzymes, and they retain critical amino acids for function, and it has been suggested that they may function by conjugating ISG17 to proteins.

A normal bovine estrus cycle is about 21 days in length. ISG17 has been detected by Day 15 of pregnancy, continuing to increase to Day 17, and remaining high through Day 26 (Hansen, T. R. et al. (1997) "Transient Ubiquitin Cross-Reactive Protein Gene Expression in the Bovine Endometrium" Endocrinology 138(11):5079-5082 and Spencer, T. E. et al. (1999) "Differential Effects of Intrauterine and Subcutaneous Administration of Recombinant Ovine Interferon Tau on the Endometrium of Cyclic Ewes" Biology of Reproduction 61:464-470). ISG17 was not detectable above background during the estrus cycle of non-pregnant bovine.

One ISG17 function is to become cross-linked to cellular proteins, as does ubiquitin. Conjugation of ISG17 to endometrial cytosolic proteins was observed by Western Blotting using a polyclonal antibody to an ISG17 polypeptide (Johnson, G. A. et al. (1998) "Pregnancy and Interferon-Tau Induce Conjugation of Bovine Ubiquitin Cross-Reactive Protein to Cytosolic Uterine Proteins" Biology of Reproduction 58:898-904). The peptide used to generate the polyclonal antibodies corresponds to amino acids 82 to 99 of ISG17. This polypeptide was chosen because it had a high antigenic index, 78% identity with ISG15, and low identity (22%) with ubiquitin. Attempts to use the antiserum to develop a pregnancy test met with limited or no success (Pru, J. K. (2000) "Regulation of bovine uterine proteins and prostaglandin F2a release by interferon-tau" Ph.D. Thesis, University of Wyoming, Appendix 1, page 1). Another antibody which has been utilized in the study of ISG17 is monoclonal antibody 5E9 (Pru, J. K. (2000) "Regulation of bovine uterine proteins and prostaglandin F2a release by interferon-tau" Ph.D. Thesis, University of Wyoming, Appendix 1).

The Johnson polyclonal antibody to ISG17 amino acids 82-89 was also used to study ISG17 induction by IFN-τ by Western blotting (Staggs, K. L. et al. (1998) "Complex Induction of Bovine Uterine Proteins by Interferon Tau" Biology of Reproduction 59:293-297).

ISG17 also can induce expression of IFN-τ in peripheral blood mononuclear cells (PMBCs) (Pru, J. K. et al. (2000)

"Production, Purification, and Carboxy-Terminal Sequencing of Bioactive Recombinant Bovine Interferon-Stimulated Gene Product 17" Biology of Reproduction 63:619-628).

Ovine UCRP (oUCRP) has been cloned (Charleston, B. and Stewart, H. J. (1993) "An interferon-induced Mx protein: cDNA sequence and high level expression in the endometrium of pregnant sheep" Gene 137:327-331). oUCRP is reported to be detectable by Day 13, and to remain high through Day 19 of ovine pregnancy (Johnson, G. A. et al. (1999) "Expression of the Interferon Tau Inducible Cross-Reactive Protein in the Ovine Uterus" Biology of Reproduction 61:312-318). Western blotting of oUCRP was performed using a polyclonal antibody to human UCRP.

Other factors, in addition to IFN-τ, may be responsible for the induction of UCRP (Johnson, G A et al. (2000) "Interferon-tau and Progesterone Regulate Ubiquitin Cross-Reactive Protein Expression in the Ovine Uterus" Biology of Reproduction 62:622-627).

All references cited herein are incorporated herein by reference in their entirety to the extent that they are not inconsistent with the disclosure herein. Citation of the above documents is not intended as an admission that any of the foregoing is pertinent prior art. All statements as to the date or representation as to the contents of these documents is based on subjective characterization of the information available to the applicant, and does not constitute any admission as to the accuracy of the dates or contents of these documents.

SUMMARY OF THE INVENTION

This invention provides methods for detecting pregnancy, for detecting non-pregnancy, and for determining readiness for breeding; immunoassay test devices and methods for making and using immunoassay test devices useful for detecting the presence and/or absence of selected IFN-τ-induced proteins; polyclonal and monoclonal antibodies to ISG-17; and methods and compositions useful for making antibodies to ISG-17.

This invention provides a method for detecting pregnancy in an ungulate or other ruminant female animal comprising: obtaining a sample from the animal and detecting the presence of a selected IFN-τ-induced protein, whereby the presence of the selected IFN-τ-induced protein indicates that the animal is pregnant. This invention also provides a method for detecting non-pregnancy in an ungulate or other ruminant female animal comprising detecting the absence of the selected IFN-τ-induced protein in the sample, whereby the absence of the selected IFN-τ-induced protein indicates that the animal is not pregnant.

This invention provides a method for determining readiness for breeding of a female animal utilizing IFN-τ-mediated signaling for maternal recognition of pregnancy comprising: detecting the absence of a selected IFN-τ-induced protein in a sample taken from the animal on a day of the animal's estrus cycle during which the presence of the selected IFN-τ-induced protein is detectable if the animal is pregnant and forcing the animal into heat or monitoring for and detecting signs of behavioral estrus.

Forcing the animal into heat can be done by means known to the art such as by giving the animal a shot of prostaglandin as described hereinbelow. Monitoring for and detecting signs of behavioral estrus is not necessary when an animal is forced into heat. The method of determining readiness for breeding provided by this invention can also include breeding the animal. Breeding can be performed by artificial or natural insemination.

The methods for detecting pregnancy and non-pregnancy and determining readiness for breeding can include using test devices, e.g. cartridge test devices and dipstick test devices, and/or other means for determining the presence or absence of a selected IFN-τ-induced protein, e.g. performing western blots, northern blots, ELISA tests, protein function tests, PCR and other assays known to the art.

This invention provides an immunoassay test device for detecting the presence of a selected IFN-τ-induced protein in a sample, the IFN-τ-induced protein being diagnostic of pregnancy in an ungulate or other ruminant animal. The device comprises a first monoclonal or polyclonal antibody specific to the selected IFN-τ-induced protein, a support for the first monoclonal or polyclonal antibody, means for contacting the first monoclonal or polyclonal antibody with the sample, and an indicator capable of detecting binding of the first monoclonal or polyclonal antibody with the selected IFN-τ-induced protein.

Detecting binding of the antibody with the selected IFN-τ-induced protein can include binding the antibody/protein complex to a second, labeled antibody which binds to the protein or to the monoclonal antibody of the complex.

Test devices can be in the form of cartridges, dipsticks, or other conformations known to the art. The test device can also be part of a kit which can contain instructions for use, instructions for comparison of test results with results of the same test done on non-pregnant animals, additional reagents, such as cells or fluids from non-pregnant animals, and other reagents known to the art.

Antibody supports are known to the art. In an embodiment of this invention, antibody supports are absorbent pads to which the antibodies are removably or fixedly attached.

The sample to be utilized for detecting pregnancy or non-pregnancy and/or for determining readiness for breeding can be obtained from an animal selected from the group consisting of ungulates and non-hoofed ruminants, including, but not limited to, cattle, sheep, goats, yak, water buffalo, bison, antelopes, gazelles, elk, reindeer, moose, bighorn sheep, giraffes, and camellids including bactrian and dromedary camels, llamas, alpacas, and vicunas. Depending on the animal, the sample can be obtained on a day selected from Day 11 to Day 32 after breeding (including any day in between). Particularly when the animal is a cow, the sample can be obtained on about Day 15 to about Day 19 to about Day 22, or to about Day 25 after breeding. When the animal is a cow, preferably the sample is obtained on about Day 18 to about Day 19 after breeding.

When certain antigens are used, the animal from which a sample is obtained is not infected with a virus, as such infection may produce levels of the selected IFN-τ-induced protein indicative of pregnancy when no pregnancy exists. This is especially true when Mx is the selected IFN-τ-induced protein.

The methods for detecting pregnancy, detecting non-pregnancy, and for determining readiness for breeding can include comparing the level of the selected IFN-T-induced protein in the sample with a background level of the selected IFN-T-induced protein in a non-pregnant animal, including an animal that has recently suffered a spontaneous abortion. This comparison can be made by any means known to the art. It can include comparing sample results with results from a second sample taken from an animal known not to be pregnant, or comparing sample results with a photograph or other representation of results from a non-pregnant animal. Comparison means can also include means for comparing levels of the selected IFN-T-induced protein in the test sample with levels present in animals which have recently aborted. Test devices having means for masking non-pregnant levels, e.g. a support having the same color or tone as indicators showing non-pregnant levels, or a filter having the same color or tone as a non-pregnant level, so that only higher, pregnant levels of a protein are detectable, e.g. by eye, can also be used. Levels of the selected IFN-T-induced protein may remain higher than normal in a non-pregnant animal following spontaneous abortion. Test devices can comprise control samples from animals that have recently aborted. The methods of this invention can include use of control samples from animals which have recently aborted as well as colored supports and/or light filters as discussed above. The above-described method steps and device means are also useful when the selected IFN-T-induced protein, such as Mx, is present at a lower level in a sample from a non-pregnant animal compared to a pregnant animal.

The selected IFN-τ-induced protein can be ISG17, Mx, GCP-2, 2',5' oligoadenylate synthetase, β2-microglobulin, IRF-1, IRF-2, 1-8U, 1-8D, Leu-13/9-27, or COX-2. The selected IFN-τ-induced protein can be an as-yet-to-be-discovered protein. In one embodiment, the selected IFN-τ-induced protein is not Mx. In another embodiment, the IFN-τ-induced protein is ISG17, Mx, IRF-1, IRF-2, 1-8U, 1-8D, or Leu-3/9-27. In another embodiment, the IFN-τ-induced protein can be ISG17 or Mx. In an embodiment, the IFN-τ-induced protein is a secreted protein like ISG17, and is present in whole blood, serum and plasma like ISG17. In another embodiment, the IFN-τ-induced protein is ISG17.

A sample can contain whole blood, plasma, serum, milk, urine, saliva and/or cells. The devices of this invention are useful for testing the above-mentioned samples. When cells are tested, the method and/or device can include a cell-lysing step or means using detergent, puncture or other physical or chemical process known to the art.

When the sample is blood, the method can also include processing the blood by a means known to the art, such as filtration or centrifugation, for separating plasma or serum which is to be assayed. This method step is especially useful when ISG17 is the selected IFN-τ-induced protein.

The methods for detecting pregnancy and non-pregnancy and for determining readiness for breeding can include performing an immunological assay using a monoclonal or polyclonal antibody to the selected IFN-τ-induced protein. Such antibodies are known to the art or can be generated by means known to the art without undue experimentation.

This invention provides methods of making monoclonal and polyclonal antibodies specific for the interferon-τ-induced protein ISG17, which is an indicator of pregnancy in ungulates and other ruminant animals. In one embodiment of this invention, antibodies are generated with, and capable of binding to, a polypeptide having an amino acid sequence selected from the group consisting of QRLAHLDSREVLQE (SEQ ID NO: 1), CQRLAHLDSREVLQE (SEQ ID NO: 2), TVAELKQQVCQKERVQ (SEQ ID NO: 3), CTVAELKQQVCQKERVQ (SEQ ID NO: 4), WLSFEGRPMDDEHPLE (SEQ ID NO: 5), and CWLSFEGRPMDDEHPLE (SEQ ID NO: 6). Other useful antibodies are made using complete or partial amino acid sequences from mammalian ISG17, Mx, GCP-2, 2',5' oligoadenylate synthetase, β2-microglobulin, IRF-1, IRF-2, 1-8U, 1-8D, Leu-13/9-27, or COX-2. Polyclonal antibodies anti-ISG27-4245, anti-ISG17-1000, specifically described hereinbelow are useful in the practice of this invention. Monoclonal antibodies made to the specific polypeptide sequences discussed above and monoclonal antibody 5E9 described hereinbelow are useful in the practice of this invention. In the devices of this invention, first antibodies can be antibodies specific to ISG17 or antibodies generated with, and capable of binding to, a polypeptide having an amino acid sequence selected from the group described above.

The method for making antibodies provided by this invention comprises providing a polypeptide of one of the foregoing amino acid sequences, administering the peptide to a mammal under conditions appropriate for stimulation of an immune response; and either isolating a polyclonal antibody from the mammal, the polyclonal antibody being capable of binding to a selected polypeptide, or isolating antibody-producing cells from the mammal, fusing the antibody producing cells with immortalizing cells to produce a hybridoma cell line, and screening the resulting hybridoma cell line to identify a cell line secreting a monoclonal antibody having a desired specificity. Other methods of making antibodies known to the art can also be used. This invention provides hybridoma cell lines and monoclonal antibodies made by the foregoing method.

This invention provides polypeptides corresponding to SEQ ID NOS: 1-6, immunogenic compositions comprising the polypeptides, and immunogenic compositions consisting essentially of the polypeptides, i.e. immunogenic compositions which will not give rise to antibodies which cross-react with other proteins not indicating pregnancy in a sample being tested to determine pregnancy of an animal. Polypeptides used to make the antibodies can be isolated from ISG17 proteins or can be synthesized by means known to the art.

This invention provides methods for determining readiness for breeding and breeding animals in a herd (i.e., a plurality of female animals) including synchronizing the estrus cycles of the animals. The method can include presynchronization (described hereinbelow), synchronization (described hereinbelow), breeding, pregnancy testing, forcing estrus, and/or rebreeding by artificial insemination.

In the devices of this invention, any indicator means known to the art to detect antibody/protein binding can be used. The indicator means can include second, labeled, monoclonal or polyclonal antibodies which bind to the selected protein, which preferably bind to a substantially different epitope on the selected protein from that to which the first monoclonal or polyclonal antibodies bind, such that binding of the first monoclonal or polyclonal antibody will not block binding of the second antibody, or vice versa. The indicator means can also include a test window through which labeled antibodies can be viewed. Any label known to the art can be used for labeling the second antibody. In an embodiment of this invention, the label is colloidal gold. The second antibody can be monoclonal or polyclonal. In an embodiment of this invention, the first antibody is monoclonal antibody 5E9 or a monoclonal antibody made to one of the specific polypeptide sequences described above, and the second antibody is a different monoclonal or polyclonal antibody which binds to a different site of ISG17, or is anti-ISG17-1000 or anti-ISG4245. In another embodiment of this invention, the first antibody is polyclonal anti-ISG17-4245 and the second antibody is anti-ISG17-1000 or the monoclonal antibody 5E9. Monoclonal antibody 5E9 has been deposited with the American Type Culture Collection, 10801 University Blvd., Manassas, Va. 20110-2209, on Nov. 3, 2006, as evidenced by Deposit Receipt dated Nov. 15, 2006, under the Budapest Treaty as ATCC Deposit No. PTA-7960. In another embodiment, the first antibody is polyclonal anti-ISG17-1000 and the second antibody is anti-ISG17-4245.

Preferably the sample to be assayed is a liquid, and the immunoassay test device is a lateral flow device comprising inlet means for flowing a liquid sample into contact with the antibodies. The test device can also include a flow control means for assuring that the test is properly operating. Such flow control means can include control antigens bound to a support which capture detection antibodies as a means of confirming proper flow of sample fluid through the test device. Alternatively, the flow control means can include capture antibodies in the control region which capture the detection antibodies, again indicating that proper flow is taking place within the device.

Methods for detecting the presence of a selected IFN-τ-induced protein using the foregoing devices are also provided, the methods comprising: providing an immunoassay test device of this invention; contacting a first antibody with a sample; and reading an indicator which is capable of detecting binding of the first antibody. Preferably, binding indicates pregnancy of the animal being tested. Methods of using these devices can be performed in the field where an animal is found, rather than requiring taking the animal or a sample from the animal to a laboratory. This on-site testing is referred to as "cowside" testing in the case of cattle.

Methods of making the immunoassay test devices of this invention are also provided, the methods comprising: supplying a first polyclonal or monoclonal antibody specific to a selected IFN-τ-induced protein; attaching the first polyclonal or monoclonal antibody to a support; providing means for contacting the polyclonal or monoclonal antibody with a sample; providing an indicator for detecting binding of the first polyclonal or monoclonal antibody to the protein; and assembling the support with the first polyclonal or monoclonal antibody attached thereto, the means for contacting the polyclonal or monoclonal antibody with a sample, and the indicator. The assembled components can be placed inside a housing, e.g. a cartridge or dipstick-style housing. Other components such as flow control means and means for comparing binding of the first polyclonal or monoclonal antibody in the sample with binding of the first polyclonal or monoclonal antibody in a second sample containing normal background levels of the IFN-τ-induced protein can also be provided and assembled in making the test devices of this invention.

Methods of making kits comprising the test devices of this invention are also provided, including, in close association, the devices, instructions for use thereof, and additional reagents required, if any.

As will be appreciated by those skilled in the art, the test devices can be made such that the first antibody is immobilized to a support, and the second, labeled antibody is not.

BRIEF DESCRIPTION OF THE DRAWINGS

In FIG. 3B, the flow control antigen is the sample antigen detection antibody.

FIG. 4A shows a result read as pregnancy. FIG. 4B shows a result read as non-pregnancy. FIG. 4C shows a result read as an uninterpretable result. FIG. 4D shows a result read as pregnancy. FIG. 4E shows a result read as non-pregnancy. FIG. 4F shows a result read as non-pregnancy.

DETAILED DESCRIPTION OF THE INVENTION

Figure 1A:
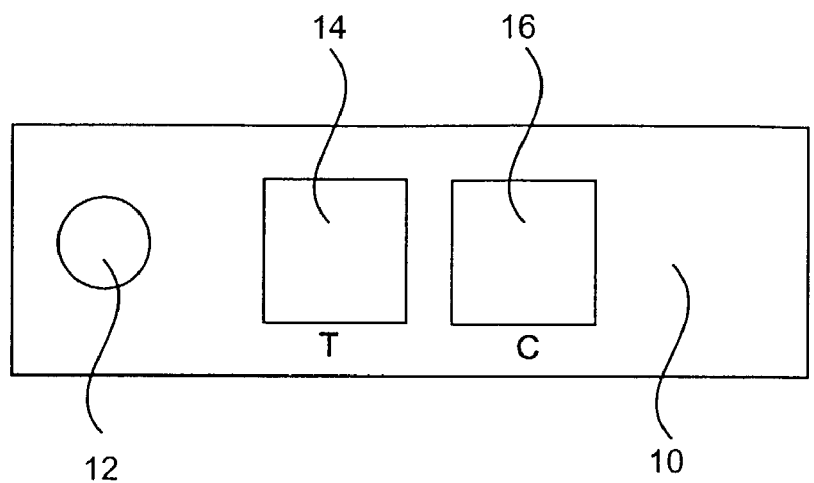
FIGS. 1A-B are top views of cartridges of this invention.

FIG. 1A illustrates a test device of this invention in cartridge (also referred to as "cassette") form. The plastic case 10 housing the test strip used for the assay is perforated with an opening 12 (also called the "sample window") in which the sample can be dropped onto the sample pad underlying the sample window. A further opening in the cassette labeled as "T" (for test) in the drawing (also called the "test window" 14) allows the user to view the area where capture antibodies have captured sample antigen/detection antibody complexes. The detection antibodies are labeled so as to be detectable through this "T" opening 14 when antigens to which they bind are present in the sample. These detection antibodies can be labeled with colloidal metals, colored latex particles, and/or other indicator compounds or conjugates known to the art which can be detected by eye or by detectors known to the art. A further opening in the cassette labeled as "C" (for control) in the drawing (also called the "control window" 16) allows the user to view the area where capture antibodies have captured control antigen/detection antibody complexes.

Figure 1B:
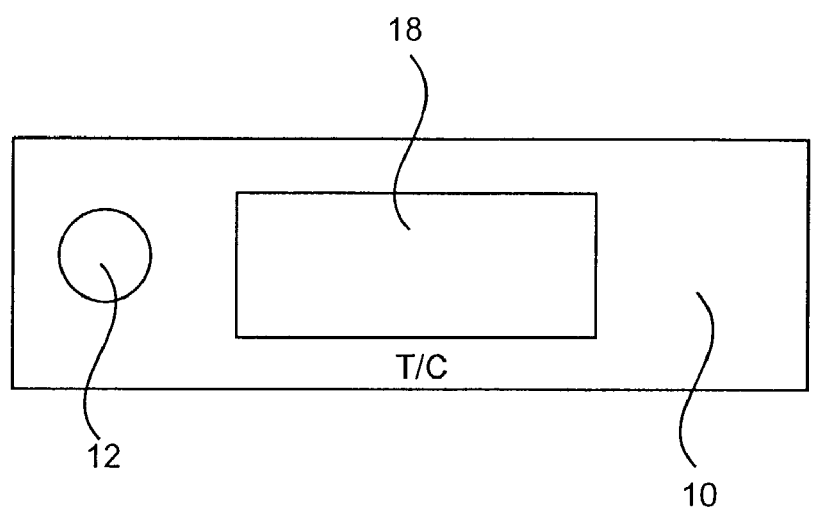

FIG. 1B illustrates a test device of this invention in cartridge (also referred to as "cassette") form. The plastic case 10 housing the test strip used for the assay is perforated with an opening 12 (also called the "sample window") in which the sample can be dropped onto the underlying sample pad. A further opening in the cassette, labeled as "T/C" (for test) in the drawing (also called the "test/control window" 18), allows the user to view the area where capture antibodies have captured sample antigen/detection antibody complexes. The detection antibodies are labeled so as to be detectable through this "T/C" opening 18 when antigens to which they bind are present in the sample. These detection antibodies can be labeled with colloidal metals, colored latex particles, and/or other indicator compounds or conjugates known to the art which can be detected by eye or by detectors known to the art. This device does not have a separate control opening. The "T/C" opening 18 also allows the user to also view the area where flow control capture antibodies have captured the detection antibody and/or control antigen/detection antibody complexes.

Figure 2A:
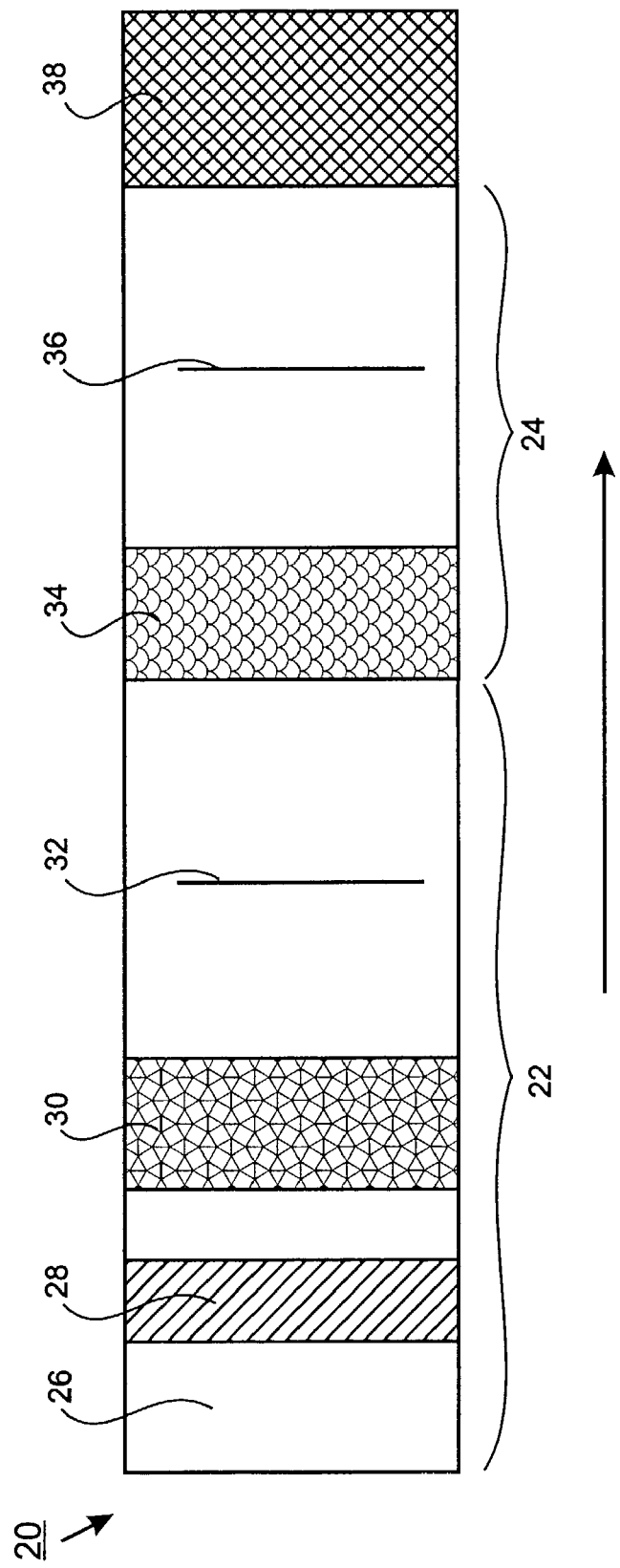
FIGS. 2A-B are schematic views of test strips for assays of this invention. The test strips can be housed within test cartridges as shown in FIGS. 1A-B.

FIG. 2A shows the inside of the test cartridge. The test strip (also referred to as a "test membrane") 20 contains a test region 22 which comprises a sample pad 26 (far left), onto which a sample fluid is dropped. A filter 28 can be arranged next to the sample pad 26 to separate contaminants in the sample, e.g. if the sample were blood, the filter would separate cell debris. Next to the filter 28 is a Detection Antibody area 30 where detection antibodies, i.e., labeled antibodies that bind the antigen or antigens being tested for, are removably placed. These antibodies are unbound to the membrane, or are so loosely bound as to be able to be carried along the test strip in the direction of flow (large arrow) of the sample. As the sample fluid passes over this area, antigen(s) in the sample being tested for become bound to their respective labeled antibodies. Next is a Capture Antibody area 32 in which antibodies to the antigen or antigens being tested for are fixedly bound. These antibodies bind and arrest the detection antibody/sample antigen complexes so that they are detectable through the test window of the cassette. In one embodiment, antibodies for the antigen being tested are laid down in a vertical line.

Following the capture antibody area, the membrane also can include a control region 24. In the control region, flow control antigens can be placed in a flow control antigen area 34, unbound to the membrane, or so loosely bound as to be able to be carried along the test strip in the direction of flow of the sample. As the sample fluid passes over this area, control antigens (which can be identical to the antigen(s) being tested for), are carried along and bound to detection antibodies in the fluid. Next to the area of control antigens is a second Capture Antibody area 36 comprising capture antibodies which can be identical to the capture antibodies in the test region bound to the membrane. These capture antibodies in the control region bind and arrest control antigen/detection antibody complexes so that they are detectable through the control window of the cassette.

When the control antigen(s) are substantially different from the antigen(s) being tested for, the control antigen(s) can be placed on the membrane upstream of the capture antibody area for the antigen(s) being tested for.

At the opposite end of the test strip 20 from the sample pad 26 is an absorbent pad 38 to maintain fluid flow through the test strip by capillary action. The arrow in FIG. 2A indicates direction of flow.

Figure 2B:
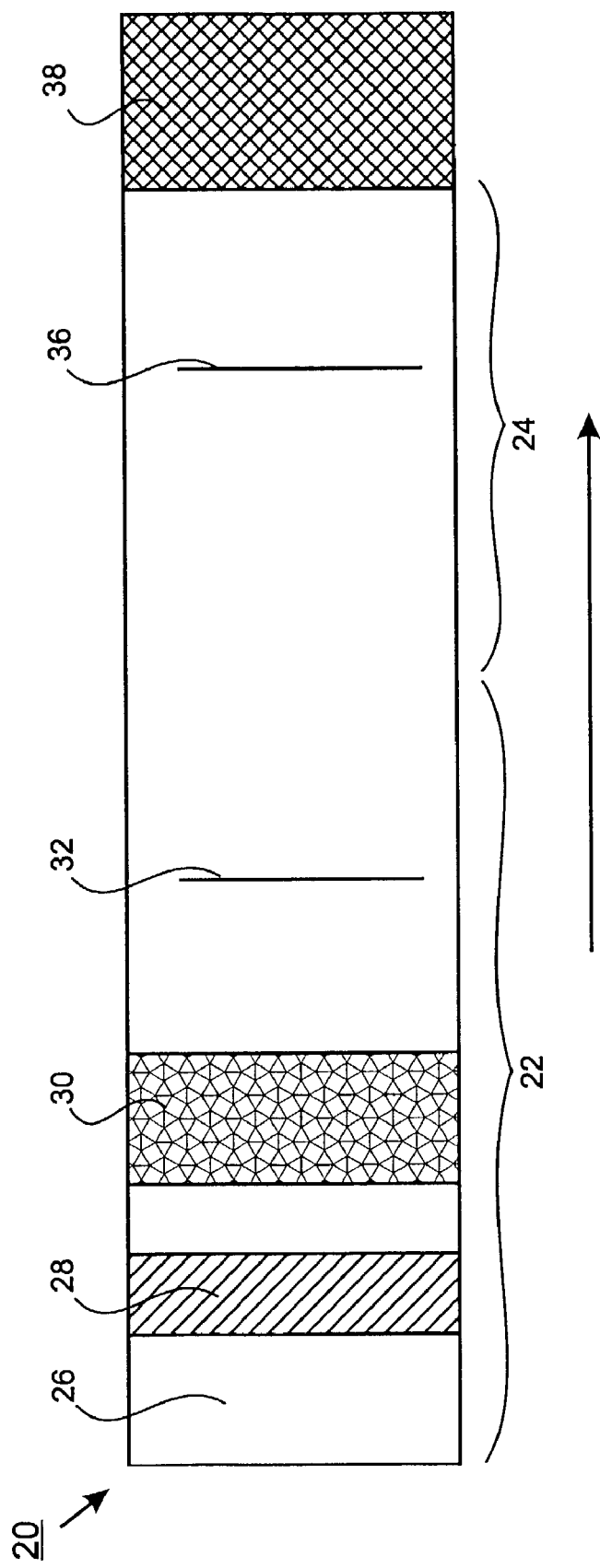

FIG. 2B also shows the inside of a test cartridge of this invention. The test strip 20 (also referred to as a "test membrane") contains a test region 22 which comprises a sample pad 26 (far left) onto which a sample fluid is dropped. A filter 28 can be arranged next to the sample pad 26 to separate contaminants in the sample, e.g. if the sample were blood, the filter would separate cell debris. Next to the filter is a Detection Antibody area 30 where detection antibodies, i.e. labeled antibodies that bind the antigen or antigens being tested for, are removably placed. These antibodies are unbound to the membrane, or are so loosely bound as to be able to be carried along the test strip in the direction of flow (large arrow) of the sample. As the sample fluid passes over this area, antigen(s) in the sample being tested for become bound to their respective labeled antibodies. Next is a first capture antibody area 32 in which antibodies to the antigen or antigens being tested for are fixedly bound. These antibodies bind and arrest the detection antibody/sample antigen complexes so that they are detectable through the test window of the cassette. In one embodiment, antibodies for the antigen being tested are laid down in a vertical line.

Following the first capture antibody area, the membrane also can include a control region 24. In the control region 24 is a flow control capture antibody area 36 comprising capture antibodies which are capable of binding to the sample antigen detection antibody. These flow control capture antibodies in the control region 24 bind and arrest sample antigen/detection antibody complexes and/or uncomplexed detection antibody so that they are detectable through the combined test/control window of the cassette.

At the opposite end of the test strip from the sample pad 26 is an absorbent pad 38 to maintain fluid flow through the test strip by capillary action. The arrow in FIG. 2B indicates direction of flow.

Figure 3A:
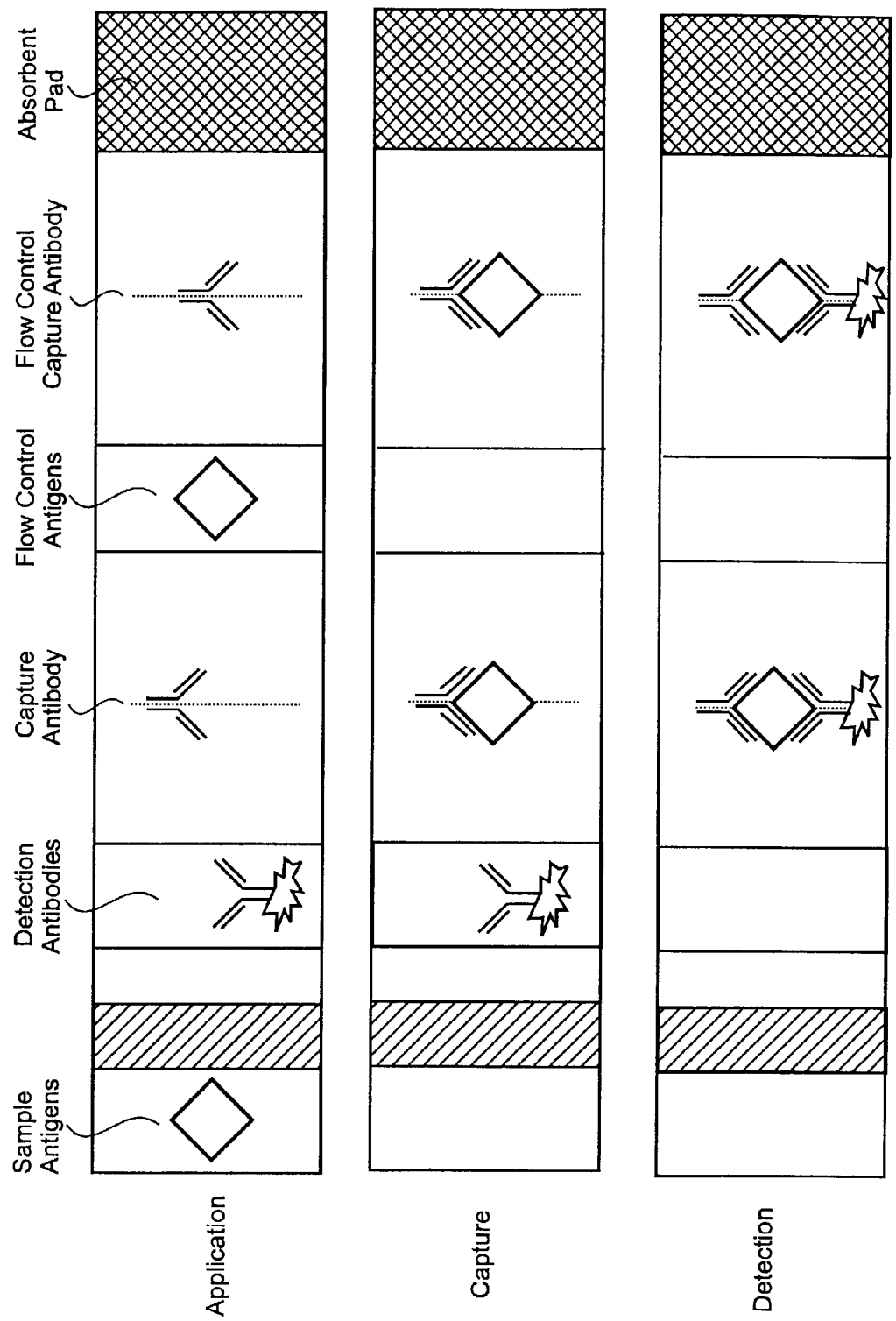
FIGS. 3A-B are schematics showing binding of antigens and antibodies at the sample application, capture, and detection stages, respectively. Both test sample antigens and flow control antigens are shown binding.

FIG. 3A shows a test strip with antigens and antibodies symbolically represented. In the top panel of FIG. 3A, the antigens are shown on the sample pad, as they would be at the beginning of an assay (Application phase) when a sample containing the IFN-τ-induced antigen (diamond) has just been applied through the sample window of a test cassette. Labeled detection Antibodies are shown in the Detection Antibody area. Capture antibodies to the IFN-τ-induced antigen are shown in the capture antibody region which lies below the test window of the cassette. Control antigens (the IFN-τ-induced antigen being tested for) are shown in the Flow Control Antigen region, and respective antibodies thereto are shown in the Flow Control Capture Antibody area of the control region which lies directly beneath the control window of the test cassette.

In the middle panel of FIG. 3A, depicting the Capture phase of the test, antigens in the sample have moved from the sample pad to the Capture Antibody area of the test region and been bound by capture antibodies. The control antigens have also been swept up by the fluid moving across the test strip and bound to capture antibodies in the Capture Antibody area of the Flow Control region.

In the lower panel of FIG. 3A depicting the Detection stage of the test, detection antibodies from the Detection Antibody area of the test region are shown as having been swept along with the sample fluid, and bound with their respective antigens, which are also bound with the respective capture antibodies in the Capture Antibody area of the test region. This panel also shows that the detection antibodies have bound with their respective control antigens and capture antibodies in the Capture Antibody area of the Flow Control region. As will be appreciated by those of skill in the art, in practice, the binding of antigens with detection antibodies and capture antibodies occurs in any order, i.e., detection antibody/antigen complexes can also be present in the Capture phase of the test.

In an embodiment of this invention, a few drops of blood are placed on the sample pad followed by a number of drops of buffer as known to the art. The sample, which may contain IFN-τ-induced antigens, is carried in the sample fluid through a filter to separate out contaminants such as cell debris or blood cells, and past a Detection Antibody area where the fluid picks up labeled detection antibodies to the IFN-τ-induced antigen being tested for. The fluid then moves to the Capture Antibody area of the test region. Capture antibodies are antibodies to the IFN-τ-induced antigen that are covalently attached to the membrane. If the capture antibodies have been laid down in a vertical line, a vertical line of labeled detection antibodies can be viewed through the test window indicating presence of the IFN-τ-induced antigen in the sample. The sample fluid then moves along the membrane strip to pick up control IFN-τ-induced antigen which has been laid down on the strip downstream of the test region. Labeled detection antibodies bind to the control antigens, and are carried downstream to the capture antibodies covalently attached to the membrane beneath the Control window. The control antigens with their attached detection antibodies are bound to the corresponding capture antibodies in the control region and indicate whether or not the test is functioning properly.

In an embodiment of this invention, a few drops of blood are placed on the sample pad followed by a number of drops of buffer as known to the art. The sample, which can contain IFN-τ-induced antigens, is carried in the sample fluid through a filter to separate out contaminants such as cell debris or blood cells, and past a Detection Antibody area where the fluid picks up labeled detection antibodies to the IFN-τ-induced antigen being tested for. The sample fluid then picks up labeled flow control antigens which are substantially different from the antigen being tested for. The fluid then moves to the Capture Antibody area of the test region. Capture antibodies are antibodies to the IFN-τ-induced antigen that are covalently attached to the membrane. If the capture antibodies have been laid down in a vertical line, a vertical line of labeled detection antibodies can be viewed through the test window indicating presence of the IFN-τ-induced antigen in the sample. The sample fluid then moves along the membrane strip and labeled flow control antigens bind to control antigens which are bound to the corresponding control capture antibodies in the control region and indicate whether or not the test is functioning properly.

The membrane can also comprises an absorbent pad at the extreme downstream end to maintain capillary action of the assay.

Figure 3B:
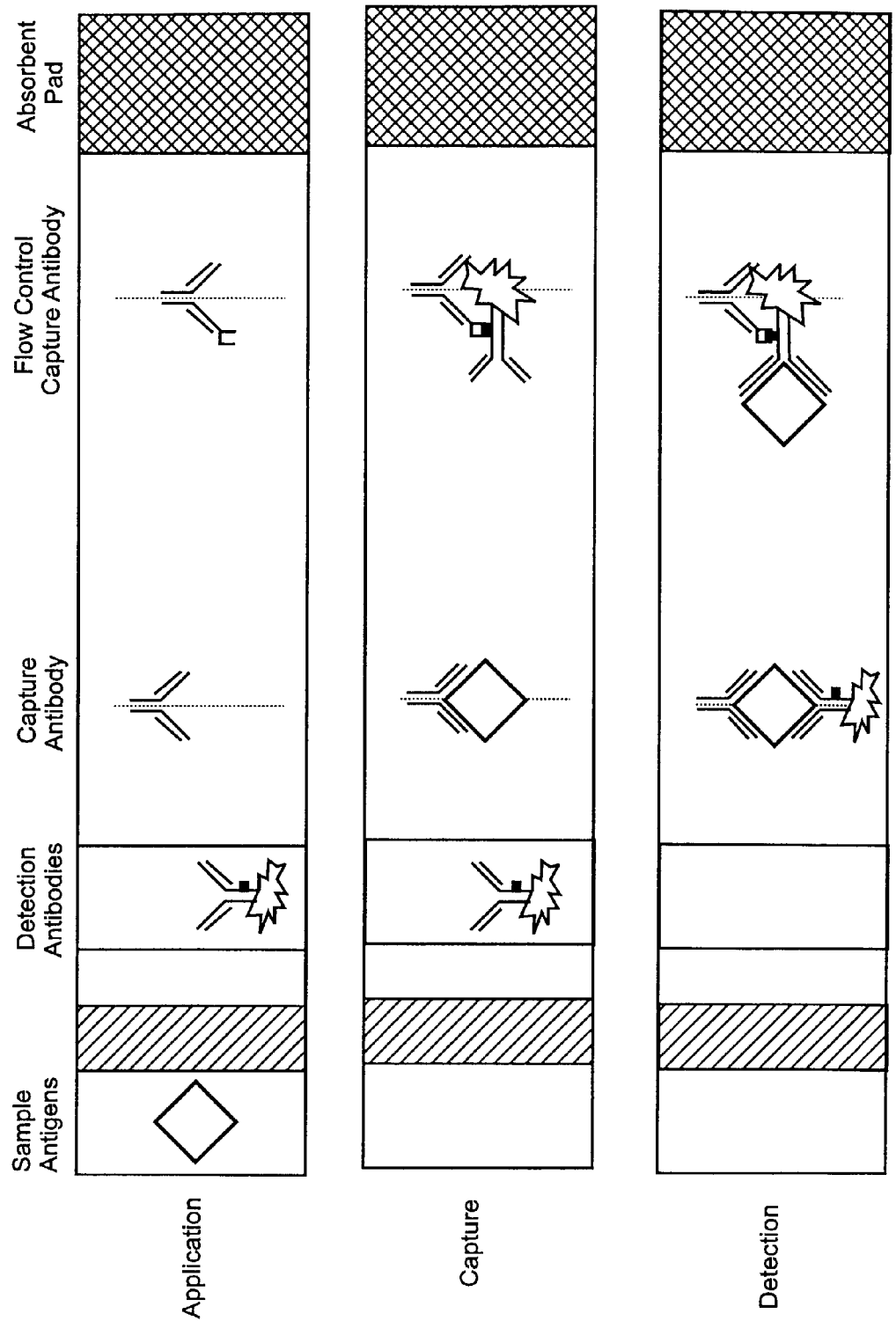

FIG. 3B shows a test strip with antigens and antibodies symbolically represented. In the top panel of FIG. 3B, the antigens are shown on the sample pad, as they would be at the beginning of an assay (Application phase) when a sample containing the IFN-τ-induced antigen (diamond) has just been applied through the sample/control window of a test cassette. Labeled detection antibodies are shown in the Detection Antibody area. Capture antibodies to the IFN-τ-induced antigen are shown in the first capture antibody region which lies below the test window of the cassette. Capture antibodies to the sample antigen detection antibodies are shown in the Flow Control Capture Antibody area of the control region which lies directly beneath the combined sample/control window of the test cassette.

In the middle panel of FIG. 3B, depicting the Capture phase of the test, antigens in the sample have moved from the sample pad to the Capture Antibody area of the test region and been bound by capture antibodies.

In the lower panel of FIG. 3B depicting the Detection stage of the test, detection antibodies from the Detection Antibody area of the test region are shown as having been swept along with the sample fluid, and bound with their respective antigens, which are also bound with the respective capture antibodies in the Capture Antibody area of the test region. This panel also shows that the flow control capture antibodies have bound with their respective antigens, the sample antigen detection antibodies, which are optionally also bound to IFN-τ-induced antigen. As will be appreciated by those of skill in the art, in practice, the binding of antigens with detection antibodies and capture antibodies occurs in any order, i.e., detection antibody/antigen complexes can also be present in the Capture phase of the test.

In an embodiment of this invention, a few drops of blood are placed on the sample pad followed by a number of drops of buffer as known to the art. The sample, which may contain IFN-τ-induced antigens, is carried in the sample fluid through a filter to separate out contaminants such as cell debris or blood cells, and past a Detection Antibody area where the fluid picks up labeled detection antibodies to the IFN-τ-induced antigen being tested for. The fluid then moves to the Capture Antibody area of the test region. First capture antibodies are antibodies to the IFN-τ-induced antigen that are covalently attached to the membrane. If the capture antibodies have been laid down in a vertical line, a vertical line of labeled detection antibodies can be viewed through the test window indicating presence of the IFN-τ-induced antigen in the sample. The sample fluid then moves along the membrane strip to the second capture antibodies, the anti-IFN-τ-induced antigen detection antibodies. Anti-IFN-τ-induced antigen detection antibodies can be any antibody which is capable of binding to antibodies produced by the mammal utilized to generate the detection antibodies. If the detection antibodies are produced in rabbits, the anti-IFN-τ-induced antigen detection antibodies can be anti-rabbit antibodies. The anti-IFN-τ-induced antigen detection antibodies can bind the detection antibodies while the detection antibodies are bound to IFN-τ-induced antigen and while they are not. Labeled detection antibodies bind to the flow control capture antibodies and indicate whether or not the test is functioning properly. The flow control capture antibodies can be before or after the IFN-τ-induced antigen capture antibodies.

The membrane can also comprise an absorbent pad at the extreme downstream end to maintain capillary action of the assay.

Figure 4A:
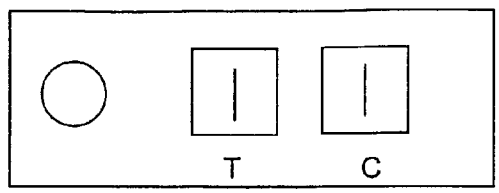
FIGS. 4A-F are top views of test cartridges of this invention showing possible outcomes of an assay of this invention.
Figure 4B:
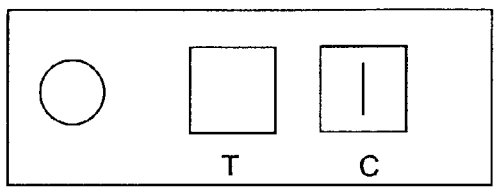
Figure 4C:
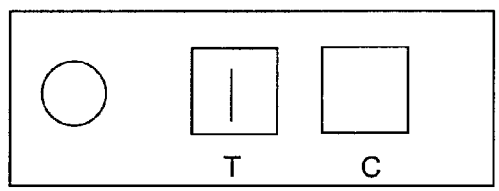

FIGS. 4A, 4B and 4C indicate the appearance of possible outcomes in the test window. In these tests, the capture antibodies beneath the test window T and the capture antibodies beneath the control window C have been laid down in a vertical line. FIG. 4A shows a result read as pregnancy. FIG. 4B shows a result read as non-pregnancy. FIG. 4C shows a result of an uninterpretable failed test in which flow through the cartridge appeared to be defective.

Figure 4D:
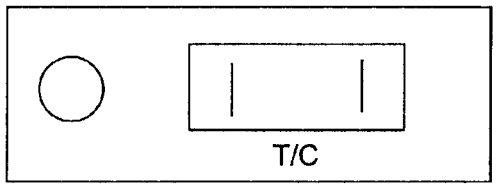
Figure 4E:
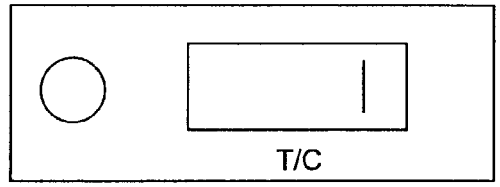
Figure 4F:
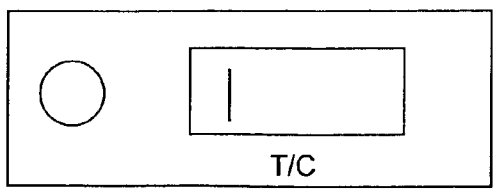

FIGS. 4D, 4E and 4F indicate the appearance of possible outcomes in the combined test/control window. In these tests, the IFN-τ-induced antigen capture antibodies and the flow control capture antibodies beneath the combined test/control window C have been laid down in a vertical line. FIG. 4D shows a result read as pregnancy. FIG. 4E shows a result read as non-pregnancy. FIG. 4F shows a result read as non-pregnancy. When there is a combined test/control window the presence of two lines is read as pregnancy and the presence of only one line, irrespective of order, is read as non-pregnancy.

Figure 5:
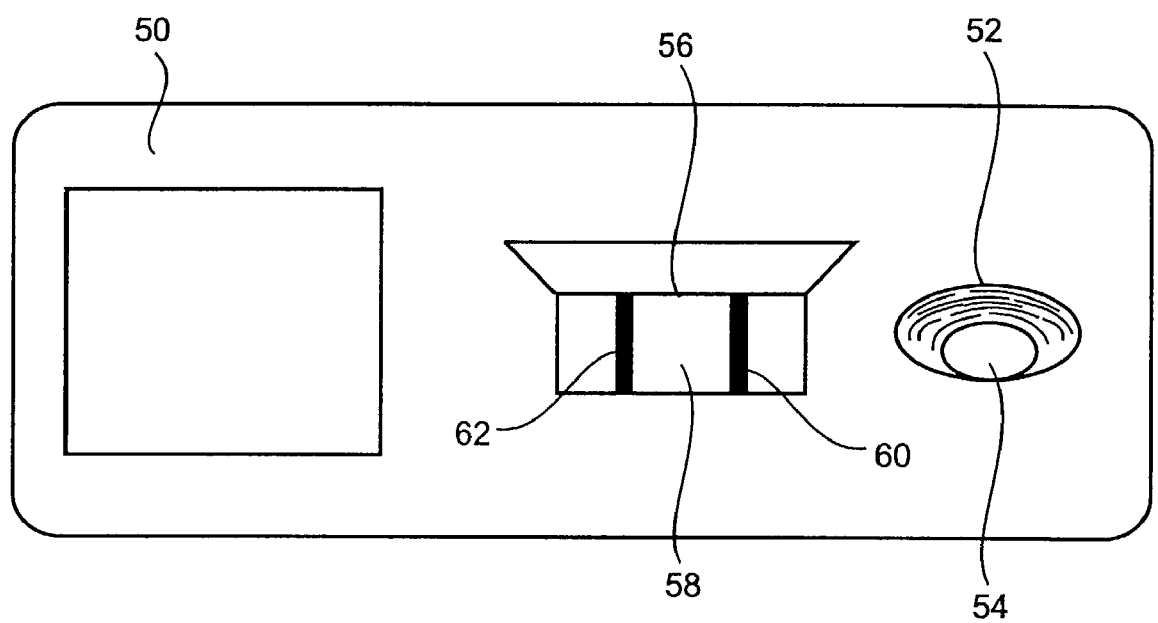
FIG. 5 is a top view of a cartridge of this invention.

FIG. 5 illustrates a test device of this invention in cartridge (also referred to as "cassette") form. The plastic case 50 housing the test strip used for the assay is perforated with an opening 52 (also called the "blood well") in which the sample can be dropped onto the underlying sample pad 54. A further opening in the cassette, labeled as "test/control result window" 56, allows the user to view the capture antibody area 58 where capture antibodies have captured sample antigen/detection antibody complexes. The detection antibodies are labeled so as to be detectable through this "test/control result window" opening when antigens to which they bind are present in the sample. These detection antibodies can be labeled with colloidal metals, colored latex particles, and/or other indicator compounds or conjugates known to the art that can be detected by eye or by detectors known to the art. The results of the flow control test are also visible in the "test/control result window" 56 allowing the user to view the area where capture antibodies have captured control antigen/detection antibody complexes. The vertical dark line 60 on the right side of the "test result window" shows the captured sample antigen/detection antibody complex. The vertical dark line 62 on the left of the "test result window" shows the captured flow control capture antibody/detection antibody complex.

The following amino acid sequences of segments of the ISG17 protein are provided herein:

```
                                            SEQ ID NO: 1
QRLAHLDSREVLQE (amino acids 43-56 of ISG17)

SEQ ID NO: 2
CQRLAHLDSREVLQE

SEQ ID NO: 3
TVAELKQQVCQKERVQ (amino acids 100-115 of ISG17)

SEQ ID NO: 4
CTVAELKQQVCQKERVQ

SEQ ID NO: 5
WLSFEGRPMDDEHPLE (amino acids 120-135 of ISG17)

SEQ ID NO: 6
CWLSFEGRPMDDEHPLE
```

DEFINITIONS

As used herein, "cow" refers to a female bovine, including a heifer.

As used herein, "first estrus cycle" refers to the estrus cycle after insemination. In cows the first estrus cycle is about 21 days following a previous estrus.

As used herein, "estrus" refers to the period during which an animal is most likely to become pregnant.

As used herein, "in heat" refers to being in the time of estrus, when an animal is most sexually receptive. In cows this period lasts about 12-18 hours.

As used herein, "behavioral estrus" refers to the behavioral demonstration that an animal is in heat, including showing standing heat.

As used herein, "standing heat" refers to the period during which a cow is receptive to a bull and will stand to be bred.

As used herein, "Day 0" is the day that an animal is in behavioral estrus or the day of breeding.

As used herein, "forcing estrus" refers to methods known in the art for forcing heat. Forcing estrus can include waiting periods, as appropriate.

As used herein, "open" refers to an animal that is not pregnant.

As used herein, "cycling" refers to an animal that is experiencing an estrus cycle, i.e., is not pregnant.

As used herein, "readiness for breeding" refers to a time in the estrus cycle when breeding is most likely to result in pregnancy.

As used herein, "breeding" refers to methods known in the art that pertain to making a female animal pregnant. Such methods include performing natural and/or artificial insemination. Breeding methods can include a waiting time after observation of behavioral estrus or after forcing estrus. In cattle, the waiting time after observing behavioral estrus is 12-18 hours. In cattle, after forcing estrus with prostaglandin on Day 18 the waiting time is 72-80 hours.

As used herein, "antibody specific to" refers to antibody that does not bind significantly to any sample components other than the desired component.

As used herein, "pregnancy testing" refers to testing for pregnancy and/or non-pregnancy.

As used herein, "whole blood" refers to blood as drawn. Whole blood contains a substantial amount of cells.

As used herein, "plasma" refers to blood with no substantial amount of cells. Plasma does contain clotting factors.

As used herein, "serum" refers to blood without a substantial amount of cells or clotting factors.

As used herein, "estrus synchronization" refers to a process whereby estrus for a group of animals is forced, such that all animals in the group are likely to ovulate within about a 3-5 day window. In cattle, injecting a group of non-pregnant cows that are in a range of cycle days, e.g. from Day 11 to 18, with prostaglandin results in estrus synchronization but not necessarily ovulation synchronization.

As used herein, "ovulation synchronization" refers to a process whereby estrus, often for a group of animals, is forced, such that all animals in the group are likely to ovulate within about a 2-3 day window. In cattle, injecting prostaglandin on Day 18 results in ovulation synchronization.

As used herein, "estrus presynchronization" refers to a process whereby the estrus cycle, often for a group of animals, is blocked or forced into a particular stage of the cycle, so that estrus or ovulation synchronization procedures that are to be performed afterwards are more successful.

As used herein, "cowside" refers to an environment in which a domesticated animal is found, particularly in contrast to a laboratory environment.

As used herein, "breeding cycle time" refers to the time between one breeding of an animal and the next breeding during the next estrus cycle of the same animal.

As used herein, "normal background level" of an IFN-τ-induced protein refers to the level of said selected IFN-τ-induced protein in a non-pregnant animal in a control sample taken during a time in an animal's estrus cycle or after breeding corresponding to the time of taking a test sample.

As used herein, "non pregnancy" refers to the state of not being detectably pregnant.

As used herein, "substantially different epitope" refers to a second binding site or set of second binding sites of a second antibody on an antigen that is different from a first binding site or set of binding sites of a first antibody on the same antigen, wherein the sites or sets of sites are sufficiently different such that the second antibody is capable of binding to the antigen simultaneously with the first antigen. A first set of binding sites of a first antibody can share binding epitopes with a second set of binding sites of a second antibody. As used herein, and as known in the art, an "epitope" refers to a single binding site of an antibody on an antigen.

This invention provides methods and compositions for testing for pregnancy and non-pregnancy in ungulates and non-hoofed ruminates. The tests provided by this invention are particularly useful during a time that coincides with the estrus cycle during which breeding occurs or the first estrus cycle after breeding of a non-pregnant animal. The tests provided by this invention are useful in estrus and ovulation synchronization programs, with pregnancy testing useful at a time allowing for resynchronization of non-pregnant animals within the first estrus cycle. The tests provided by this invention assay for the presence, absence, or particular level of a selected IFN-τ-induced protein in a sample from a female animal. The tests of this invention are useful for testing cells, blood, plasma, serum, cells, milk, nasal secretions, ocular secretions, vaginal secretions, urine, and saliva samples. The tests provided by this invention are immunoassays. Polyclonal and monoclonal antibodies useful in such tests, as well as methods of making such antibodies and hybridoma cell lines, are provided. Devices for performing such tests, methods of using such devices, and methods of making such devices are provided. Kits containing such devices are also provided. This invention provides a method for determining readiness for breeding. This invention provides a method for resynchronizing breeding with breeding cycle times of one estrus cycle or shorter. This invention also provides a method for breeding by forcing estrus and artificial insemination by appointment.

The immunoassays of this invention can be lateral flow, sandwich assays. The detection mechanism can be colloidal gold. The tests of this invention can be designed to be performed cowside, in a format such as a cartridge or a dipstick. Many fluids, cells, and tissues, such as whole blood, plasma, serum, urine, milk, nasal secretions, ocular secretions, vaginal secretions, and saliva are useful in the practice of this invention. In one embodiment, the sample is blood, plasma, or serum. The tests of this invention are useful on all female animals utilizing IFN-τ as the sole signal, or as one of many signals, for the maternal recognition of pregnancy. Animals suitable for the methods of this invention include ungulates and other ruminants. Ungulates that are ruminants include: cattle, sheep, goats, yak, water buffalo, and bison. Non-domesticated ungulates include: antelopes, gazelles, elk, reindeer, moose, bighorn sheep, giraffes, and other members of the cattle, sheep and goat families. Ruminant non-ungulates include: bactrian and dromedary camels and other camellids, such as llamas, alpacas, and vicunas. Ungulate non-ruminants include domesticated and non-domesticated swine and horses. The tests of this invention are useful for testing ungulates and non-hoofed ruminants, for testing ungulate and non-hoofed ruminant domesticated animals, and for testing bovine and ovine animals. Ungulates and non-hoofed ruminants include members of Artiodactyla, and Perissodactyla. The methods and compositions of this invention are useful for any of the above-mentioned animals that can become pregnant. In bovines such animals are heifers, dairy cows, and beef cattle.

Immunoassay devices are known to the art and are made by companies such as Millipore (Billerica, Mass., USA) and Arista (Fremont Calif., USA) and can be modified in accordance with the teachings hereof by one of ordinary skill in the art without undue experimentation.

IFN-τ-induced proteins are divisible into classes. Class 1 comprises all IFN-τ-induced proteins (induced directly and indirectly). Class 2 comprises all IFN-τ-induced proteins of Class 1 that are detectable in non-pregnant animals but are detectable at levels substantially above background levels in pregnant animals, such as Mx. Class 3 comprises all IFN-τ-induced proteins of Class 1 that are secreted, including ISG17. Class 4 comprises all IFN-τ-induced proteins of Class 1 that are detectable in whole blood. Class 5 comprises all IFN-τ-induced proteins of Class 4 that are detectable in plasma, such as ISG17. Class 6 comprises all IFN-τ-induced proteins of Class 1 excluding Mx. Class 7 comprises all IFN-τ-induced proteins of class 1 which are detectable only in pregnant animals, such as ISG17, 1-8U, and Leu-13/9-27. Class 1 includes, but is not limited to, ISG17, Mx, GCP-2, 2',5' oligoadenylate synthetase, β2-microglobulin, IRF-1, IRF-2, 1-8U, 1-8D, Leu-13/9-27, and COX-2. The methods and compositions of this invention are useful for testing Class 1, Class 2, Class 3, Class 4, Class 5, Class 6, and Class 7 IFN-τ-induced proteins. In one embodiment, the IFN-τ-induced proteins utilized in the methods and compositions of this invention are of Class 5. In another embodiment, the IFN-τ-induced protein is ISG17.

The tests provided in this invention can be immunoassays or other testing methods known in the art that are useful for measuring IFN-τ-induced protein levels, either directly or indirectly, such as western blot, sandwich blot, ELISA, dot blot, slot blot, Northern blot, PCR, and antibody precipitation, are useful in the methods of this invention. In one embodiment, the immunoassays of this invention are sandwich immunoassays, but other types of immunoassays, such as Western blots are useful. In one embodiment, one of the antibodies is labeled. Other detection methodologies are useful in the practice of this invention. The sandwich assays provided by this invention can utilize polyclonal and/or monoclonal antibodies to the selected IFN-τ-induced protein. They can use the same or different polyclonal or monoclonal antibodies for capture and detection. Preferably they utilize two different antibodies. The antibody or antibodies are divided into two categories, detection and capture. The detection antibody can be labeled with a label known to the art. In an embodiment of this invention, the label is colloidal gold. In one embodiment the sandwich assay is performed using a device, such as a cartridge or a dipstick. The devices provided by this invention comprise detection and capture antibodies, support for the antibodies, a means for contacting the antibodies with a sample from an animal, a means of detecting binding of the antibodies to the selected IFN-τ-induced protein, and optionally flow control elements to confirm that the sample is properly flowing within the test device. The devices can also contain a means for measuring the level of the selected IFN-τ-induced protein relative to the amount of background level, in a non-pregnant animal, of the selected IFN-τ-induced protein. Some of the devices also contain a means for lysing cells. Some of the devices also contain a means for filtering serum or plasma from whole blood. When the selected IFN-τ-induced protein is ISG17, the antibodies can be chosen from polyclonal antibodies anti-ISG17-4245 (Example 10) and anti-ISG17-1000 (Example 12), and monoclonal antibody 5E9. In an embodiment of this invention, anti-ISG17-1000 is the capture antibody and anti-ISG17-4245 is the detection antibody.

An embodiment of this invention is a device that contains a sample window for the placement of the sample, and test and control windows where the test results are read. When the sample is placed in the sample window, a support absorbs liquid from the sample. The sample window and absorbent support provide means for contacting the antibodies with the sample. The detection antibody that was previously removably placed on the support is resuspended in the sample liquid. Components of the flow control can also be resuspended. If the selected IFN-τ-induced protein is substantially present in the sample liquid, the detection antibody will bind. As the sample liquid flows laterally down the support, the sample liquid passes the capture antibody, which has been immobilized on a support beneath the test window. If the selected IFN-τ-induced protein is substantially present, it will be bound to the detection antibody and will also bind to the capture antibody. The selected IFN-τ-induced protein can also bind to the capture antibody before being bound by the detection antibody. A sandwich of capture antibody, antigen, and detection antibody will be present under the test window. When the detection antibody has been labeled with colloidal gold, a dark line of colloidal gold will appear in the test window as a result of the sandwich. As the liquid continues to flow past the capture antibody, whether or not a sandwich is formed, the liquid, which can contain resuspended flow control components, reaches flow control components that are immobilized in the control window. As the sample liquid passes by the immobilized flow control components, a dark line appears in the control window. An example of flow control means is shown in FIG. 2A. Flow control antigens are removably placed on the support before or after the selected IFN-τ-induced protein capture antibody but before anti-flow-control-antigen-antibodies are immobilized. If the flow control antigens are substantially different from the antigens to be tested they can be placed upstream, but if they are not substantially different, they must be placed downstream. The appearance of a dark line beneath the flow control window correlates with liquid flowing by. The test results are readable in less than or about five minutes. The test results are read by observing the presence or absence of dark lines in the test and/or control windows. The appearance of a line in both the test window and the control window signifies pregnancy, and the animal is deemed pregnant. The appearance of a line in only the control window signifies non-pregnancy and the animal is deemed not pregnant. The appearance of a line only in the test window or the appearance of no lines at all signifies a defective test. The test, using a new device, can be repeated.

Another embodiment of this invention is a device that contains a sample window for the placement of the sample, and a combined test/control window where the test results are read. When the sample is placed in the sample window, a support absorbs liquid from the sample. The sample window and absorbent support provide means for contacting the antibodies with the sample. The detection antibody that was previously removably placed on the support is resuspended in the sample liquid. If the selected IFN-τ-induced protein is substantially present in the sample liquid, the detection antibody will bind. As the sample liquid flows laterally down the support, the sample liquid passes the IFN-τ-induced protein capture antibody, which has been immobilized on a support beneath the test/control window. If the selected IFN-τ-induced protein is substantially present, it will be bound to the detection antibody and will also bind to the capture antibody. The selected IFN-τ-induced protein can also bind to the capture antibody before being bound by the detection antibody. A sandwich of capture antibody, antigen, and detection antibody will be present under the test/control window. When the detection antibody has been labeled with colloidal gold, a dark line of colloidal gold will appear in the test window as a result of the sandwich. As the liquid continues to flow past the capture antibody, whether or not a sandwich is formed, the liquid containing detection antibody reaches the immobilized flow control capture antibody. A dark line appears in the combined test/control window when the flow control capture antibody binds to the unbound labeled detection antibody or the bound labeled detection antibody/IFN-τ-induced protein complex. An example of flow control means is shown in FIG. 2B. The appearance of a dark line beneath the test/control window correlates with liquid flowing by. The test results are readable in less than or about five minutes. The test results are read by observing the presence or absence of dark lines in the test/control window. The appearance of two lines in the test/control window signifies pregnancy, and the animal is deemed pregnant. The appearance of only one line in the test/control window signifies non-pregnancy and the animal is deemed not pregnant. The appearance of only one line can be the result of non-pregnancy or a defective test. The test, using a new device, can be repeated.

Some IFN-τ-induced proteins, such as Mx, may be present in samples of non-pregnant animals at lower levels than in pregnant animals. Devices useful for testing for pregnancy using such proteins can include means for comparing the level of the selected IFN-τ-induced protein in the sample being tested with the level of the same IFN-τ-induced protein in a non-pregnant animal. Such comparison means include test supports comprising the same antibodies and labels which have previously been contacted with a sample from a non-pregnant animal. Such comparison means can also include a picture showing the appearance of such a test result from a non-pregnant animal. Such comparison means can also include the use of supports having a color identical to the color produced by testing a non-pregnant animal, so that such test results are not detectable by eye, and only a stronger color produced by testing a pregnant animal can be detected. Similarly, a filter having a color masking detection of binding produced by testing a non-pregnant animal, but allowing the stronger color of binding produced by testing a pregnant animal to be seen, can be provided as such comparison means. The tests of this invention can be performed with a sample containing any cell in which the selected IFN-τ-induced protein is found or in any bodily fluid in which the selected IFN-τ-induced protein is found. Preferably, the test does not substantially increase the risk of spontaneous abortion in a pregnant animal, as do tests involving removal of endometrial tissue. Cells, tissues, and fluids useful in the methods of this invention include whole blood, plasma, serum, urine, milk, nasal secretions, ocular secretions, vaginal secretions, and saliva. In one embodiment blood, plasma, or serum is utilized in the practice of this invention.

The tests of this invention are performed at a time after breeding when the presence of a selected IFN-τ-induced protein would indicate pregnancy. Depending on the animal, the sample can be obtained on a day selected from about Day 11 to about Day 32 after breeding (including any day in between). When the animal is a cow, the sample can be obtained from about Day 15 to about Day 19 or to about Day 22 or to about Day 25 after breeding. In an embodiment of this invention, the sample is obtained at Day 18 after breeding. In bovines, ISG17 is detectable using the methods and compositions of this invention at about Day 11 until about Day 32 of pregnancy. The tests of this invention can be performed during the window of an estrus cycle in which methods for forcing estrus, such as by providing single injections of prostaglandin, are effective during that estrus cycle, but late enough in the cycle that the greatest number of naturally occurring spontaneous abortions will have occurred. In cows, the tests can be performed at about Day 18. A single injection of prostaglandin, such as a 5 cc injection of prostaglandin $PGF_2\alpha$ (Lutalyse, Pharmacia Upjohn, Peapack, N.J.), is effective for forcing estrus when a mature corpus luteum is available, such as during Day 18 of the bovine estrus cycle. In bovines, when the IFN-τ-induced protein is ISG17, the tests can be performed during Days 14-32 after breeding, during Days 15-25, during Days 15-22, during Days 18-19, and/or during Day 18.

Each species of ungulate and other ruminant animals has an estrus cycle of a particular average length. The estrus cycles of ungulate and other ruminant animals are known. In cows the estrus cycle is about 21 days. In sheep the estrus cycle is about 17 days. The time in the estrus cycle when IFN-τ-induced proteins are detectable consequently varies accordingly for each species. For example, ISG17 is detectable in cows as early as Day 11, and in sheep it is detectable slightly earlier. The times during which IFN-τ-induced proteins of this invention are detectable by the methods of this invention vary for each species. These times are known to the art or can be determined by one of ordinary skill in the art without undue experimentation.

In the methods of this invention, female animals can be presynchronized by any method known to the art including but not limited to Presynch or MGA™. After presynchronization, animals can be synchronized by any method known to the art, including, but not limited to, Ovsynch, in preparation for timed artificial insemination. Animals can be watched for behavioral estrus. Breeding can be performed by any method known to the art. In one embodiment, animals are bred by artificial insemination by appointment, at a time appropriate for the selected species and synchronization protocol. At a time appropriate for each species, about Day 18 in cattle, animals are tested for pregnancy using the compositions and methods of this invention. Animals determined to be not pregnant are readied for breeding. Readying for breeding can involve waiting and watching for behavioral estrus. In one embodiment, readying involves forcing estrus. Readying for breeding can involve injecting prostaglandin, such as LUTALYSE® containing 25 mg of $PGF_{2\alpha}$. Forcing of more than one animal at once allows for synchronization of the animals. Estrus and ovulation can be forced, at an appropriate time for each species and forcing method, such as on about Day 18 in cattle, such that estrus and ovulation are synchronized to allow for AI by appointment, at 36-80 hours, or 72-80 hours, following prostaglandin injection. Animals can be bred by any method known in the art, including by TAI. For the second time, at a time appropriate for each species, animals are tested for pregnancy using the compositions and methods of this invention. This cycle of breeding, pregnancy testing, forcing estrus and/or ovulation, and breeding, is continued until a satisfactory number of animals are determined to be pregnant. Practicing this cycle allows animals to be made pregnant in a minimum amount of time. The second round of breeding can occur within or at the end of the timing of a normal estrus cycle.

The methods of this invention are an improvement over Resynch programs. Previously, Resynch programs have been limited to methods of testing for pregnancy not including assays for IFN-τ-induced proteins. By pregnancy testing at an appropriate time, such as Day 18 in cattle, using the compositions and methods of this invention, animals can be resynchronized at an optimal time in the estrus cycle, allowing animals to be rebred in a shorter amount of time than was previously possible.

The methods and compositions of this invention are useful for testing for pregnancy in animals that are not infected by virus, or for testing for pregnancy in animals that are infected by virus when the selected IFN-τ-induced protein is not substantially induced by viral infection in the sample tested.

The methods and compositions of this invention are useful for testing for pregnancy in animals that have not experienced spontaneous abortion within a previous period during which the IFN-τ-induced protein remains elevated over non-pregnant levels, e.g., the previous five days.

The methods and compositions of this invention are useful for detecting ISG17 in conjugated as well as non-conjugated forms.

The methods and compositions of this invention are particularly useful for diagnosing the pregnancy status of AI herd cows (herds of cows that have been artificially inseminated). The methods and compositions of this invention are an improvement to AI and resynchronization programs. The invention provides the ability to diagnose pregnancy in a cow from Days 18-19 post AI, allowing re-insemination within the same estrus cycle as the initial breeding for cows that did not get pregnant.

Two types of cows are artificially inseminated. The first type are naturally coming in and out of behavioral estrus, a phase which lasts about 12-18 hours, requiring intense observation by dairy farmers and breeders. If behavioral estrus is not observed and the cow is not artificially inseminated, the breeding window is missed and the cow will not return to estrus for about 21 days. The methods and compositions of this invention are useful to natural breeders. On Day 0 a cow in heat is observed. On Day 0, within 12-18 hours of the first observation of heat, the cow is artificially inseminated. On a day within Days 18-19 the methods and compositions of this invention are utilized to determine the pregnancy status of the cow. If the cow is determined to be non-pregnant (open), the breeder can wait until about Day 21 and watch for behavioral estrus and artificially inseminate again, or give the cow an injection of prostaglandin and artificially inseminate again within 80 hours, thus keeping the cow in the same or first 21-day cycle.

The second type of artificially inseminated cow is a cow that is forced into estrus to be bred by appointment. This process is used by time breeders in synchronization programs. This process does not require a breeder to watch for behavioral estrus, because GnRH and prostaglandin are used to synchronize the estrus cycle and trigger ovulation. The methods and compositions of this invention can be utilized by these breeders. An example of the process begins with a presynchronizing injection of prostaglandin to ensure that the cow has a corpus luteum (about 24 days before artificial insemination (AI) is planned). After 14 days, an injection of GnRH is given to start a new follicle wave (about 10 days before AI). After 7 days, a second or breeding injection of prostaglandin is given (about three days before AI). The cow is then artificially inseminated on observation of behavioral estrus or on the morning of the third day following the breeding injection if behavioral estrus is not observed. At Day 18 after AI, the pregnancy status of the cow is determined, using the methods and compositions of this invention. Prostaglandin injections are given to cows determined to be not pregnant or open. These cows are then artificially inseminated again within 80 hours, which is within the 21-day window of the first estrus cycle. Using this process, the number of cows in a herd that are re-inseminated will increase about 50%.

Without the compositions and methods of this invention, it is not possible to reliably determine the pregnancy status of a cow within the 21-day window of the first estrus cycle. Further, the methods and compositions of this invention allow for reliable determination of pregnancy status early enough in the 21-day window that the cow can be resynchronized in time for the next estrus.

Visual signs of behavioral estrus (also called "standing heat") include riding of other cows, roughened hair or hair rubbed off on the tailhead indicating that the cow has been ridden by other animals, behavior such as following others, standing close and sniffing, nuzzling and licking another animal's back or rump. Cows in heat or near onset of heat tend to group together. They are generally more nervous than usual, and may bawl considerably, pace the fence and seem restless. Keen observers, familiar with their animals, often can tell cows in or approaching heat by subtle changes in normal appearance. A drop in milk production sometimes is observed. Another good indicator is stringy, clear (egg white appearance) mucus hanging from the vulvar opening or smeared on the tail or buttocks. Clear mucus discharges often can be seen in the gutter or on the ground where a cow had been resting. The vulvar lips will look moist and slightly swollen. A somewhat smoother surface is shown rather than the normal dry, finely wrinkled vulvar lips of a non-estrous cow. Further, the hairs of a cow in heat tend to be wet and matted and smeared by tail-rubbing activity. Bloody mucus, although not a consistent sign, can be observed between the second and fourth days following heat. This is not a sign of heat, but indicates the animal was in heat several days ago. Accurate detection can involve periods of observation of thirty minutes twice a day. Many devices to assist with heat detection are available on the market. Monitoring for visual signs of behavioral estrus is optional when estrus is forced.

Monoclonal and polyclonal antibodies specific for IFN-τ-induced proteins are particularly useful in the practice of this invention. Monoclonal antibodies useful in this invention are obtained by well-known hybridoma methods (Harlow and Lane (1988) Antibodies: A Laboratory Manual, Cold Spring Harbor Laboratories; Goding (1986) Monoclonal Antibodies: Principles and Practice, 2d ed., Academic Press, New York; and Ausubel et al. (1993) Current Protocols in Molecular Biology, Wiley Interscience/Greene Publishing, New York, N.Y.). An animal is immunized with a preparation containing IFN-τ-induced proteins or peptides. A fused cell hybrid is then formed between antibody-producing cells from the immunized animal and an immortalizing cell such as a myeloma.

The monoclonal anti-IFN-τ-induced protein antibodies can be produced in large quantities by injecting anti-IFN-τ-induced protein antibody-producing hybridoma cells into the peritoneal cavity of mice and, after an appropriate time, harvesting ascites fluid from the mice which yield a high titer of homogenous antibody. The monoclonal antibodies are isolated therefrom. Alternatively, the antibodies can be produced by culturing anti-IFN-τ-induced protein antibody producing cells in vitro and isolating secreted monoclonal anti-IFN-τ-induced protein antibodies from the cell culture medium directly.

Another method of forming antibody-producing cells is by viral or oncogenic transformation. For example, a B-lymphocyte which produces an IFN-τ-induced protein specific antibody can be infected and transformed with a virus, such as the Epstein-Barr virus, to give an immortal antibody-producing cell (Kozbon and Toder (1983) Immunol. Today 4:72-79).

Polyclonal antibodies can be prepared by immunizing an animal with a crude preparation of the anti-IFN-τ-induced protein or peptide, the purified anti-IFN-τ-induced protein or peptide or a synthesized anti-IFN-τ-induced protein or peptide. The animal is maintained under conditions whereby antibodies reactive with the components of the complex are produced. Blood is collected from the animal upon reaching a desired titer of antibodies. The serum containing the polyclonal antibodies (antisera) is separated from other blood components. The polyclonal antibody-containing serum can optionally be further separated into fractions of particular types of antibodies (e.g., IgG or IgM) or monospecific antibodies can be affinity purified from polyclonal antibody containing serum.

The present invention provides a kit comprising an antibody preparation that binds immunologically to an IFN-τ-induced protein and a suitable container therefore. The kit can further comprise a second antibody preparation that binds to the same IFN-τ-induced protein (wherein the second antibody binds a different epitope unless the detected protein is a dimer or larger polymer). The first antibody can be removably attached to a support and comprises a detectable label. The detectable label can be any label known in the art including but not limited to a fluorescent tag, a chemiluminescent tag, an enzyme, or colloidal gold. In one embodiment, the label is colloidal gold. If the label is an enzyme, the kit can further contain substrate for the enzyme. The support can be any support routinely used in immunological techniques. The container can be a polystyrene plate, cartridge, test tube, or dipstick. The second antibody preparation can comprise detectable label. The kit can further comprise a buffer or diluent, and a suitable container therefor. As is known in the art, assays using immobilized detection antibodies can also be used.

Other kit components, including reagent reservoirs, instructions, and the like are well known to those of skill in the art, and are contemplated for use in the kits described herein.

The present invention utilizes antibodies in the immunologic detection of IFN-τ-induced proteins. Various useful immunodetection methods have been described in the scientific literature, such as Nakamura et al. (1987). Immunoassays, in their most simple and direct sense, are binding assays. Useful immunoassays are the various types of antibody-conjugated assays, including colloidal gold-conjugated assays and enzyme linked immunosorbent assays (ELISAs), and radioimmunoassays (RIA). Immunochemical detection using tissue sections also is particularly useful. However, it will be readily appreciated that detection is not limited to such techniques, and Western blotting, dot blotting, FACS analyses, and the like also can be used in connection with the present invention.

In general, immunobinding methods include obtaining a sample suspected of containing a protein, peptide, or antibody, and contacting the sample with an antibody or protein or peptide in accordance with the present invention, as the case may be, under conditions effective to allow the formation of immunocomplexes.

Contacting the chosen biological sample with the protein, peptide, or antibody under conditions effective and for a period of time sufficient to allow the formation of immune complexes (primary immune complexes) is generally a matter of simply adding the composition to the sample and incubating the mixture for a period of time long enough for the antibodies to form immune complexes with the IFN-τ-induced proteins. During or after this time, the IFN-τ-induced protein-antibody mixture is washed to remove any non-specifically bound antibody species, allowing only those antibodies specifically bound within the primary immune complexes to be detected.

In general, the detection of immunocomplex formation is well known in the art and can be achieved through the application of numerous approaches. These methods are generally based upon the detection of a label or marker, such as any radioactive, fluorescent, biological, enzymatic tags, colloidal gold, or labels of standard use in the art. U.S. patents concerning the use of such labels include U.S. Pat. Nos. 5,360,895; 3,817,837; 3,850,752; 3,939,350; 3,996,345; 4,277,437; 4,275,149; and 4,366,241. Of course, one can find additional advantages through the use of a secondary binding ligand such as a second antibody or a biotin/avidin ligand binding arrangement, as is known in the art.

The primary immune complexes can be detected by means of a second binding ligand that has binding affinity for the IFN-τ-induced protein or the IFN-τ-induced protein specific first antibody. In these cases, the second binding ligand can be linked to a detection label. The second binding ligand is itself often an antibody, which can thus be termed "secondary" antibody. The primary immune complexes are contacted with the label, secondary binding ligand, or antibody, under conditions effective and for a period of time sufficient to allow the formation of secondary immune complexes. The secondary immune complexes are coincidentally or later generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the IFN-τ-induced protein or anti-IFN-τ-induced protein antibody is used to form secondary immune complexes as described above. The second binding ligand contains an enzyme capable of processing a substrate to a detectable product and, hence, amplifying signal over time. After washing, the secondary immune complexes are contacted with substrate, permitting detection.

As a part of the practice of the present invention, the principles of an enzyme-linked immunoassay (ELISA) can be used. ELISA was first introduced by Engvall and Perlmann (1971) and has become a powerful analytical tool using a variety of protocols (Engvall (1980), Engvall (1976), Engvall (1977), Gripenberg et al. (1978), Makler et al. (1981), and Sarngadharan et al. (1984). ELISA allows for substances to be passively adsorbed to solid supports such as plastic to enable facile handling under laboratory and field conditions. For a comprehensive treatise on ELISA, the skilled artisan is referred to "ELISA: Theory and Practice" (Crowther, 1995).

In one embodiment, the invention comprises a "sandwich" ELISA, where anti-IFN-τ-induced protein antibodies are immobilized onto a selected surface, such as a well in a polystyrene microtiter plate, cassette, or dipstick. Then, a test sample suspected of containing IFN-τ-induced proteins is contacted with the surface. After binding and washing to remove non-specifically bound immunocomplexes, the bound antigen can be detected by a second antibody to the IFN-τ-induced protein.

Alternatively, polypeptides from the sample can be immobilized. Antibody competition can be used. Irrespective of the format used, ELISAs have certain features in common, such as coating (to prevent non-specific binding), incubating or binding, washing to remove non-specifically bound species, and detecting the immune complexes. It is common to use a secondary or tertiary detection means, rather than a direct procedure. Detection of the immune complex then requires a labeled secondary binding ligand or antibody, or a secondary binding ligand or antibody in conjugation with a labeled tertiary antibody or third binding ligand. The associated label can generate a color development upon contact with an appropriate chromogenic substrate.

A variant of ELISA is the enzyme-linked coagulation assay or ELCA (U.S. Pat. No. 4,668,621). In this system, the reactions can be performed at physiological pH in the presence of a wide variety of buffers.

In the practice of this invention, the first antibody to an IFN-τ-induced protein can be labeled with colloidal gold, the second antibody, which can be the same as the first, recognizing the same IFN-τ-induced protein, is immobilized. Washing occurs simultaneously with binding. Detection results from aggregation of gold.

EXAMPLES

Example 1

A cycling cow is given an injection of prostaglandin, such as 5 cc of LUTALYSE® Sterile Solution (Pharmacia, Peapack, N.J.). Fourteen days later, the cow is given an injection of gonadotropin releasing hormone (GnRH). Seven days later, the cow is given a second, breeding injection of prostaglandin. Behavioral estrus is observed on the second day. The cow is bred. Eighteen days later, the cow is tested for pregnancy using the compositions and methods of this invention.

Example 2

A cycling cow is given an injection of prostaglandin, such as 5 cc of LUTALYSE® Sterile Solution (Pharmacia, Peapack, N.J.). Fourteen days later, the cow is given an injection of GnRH. Seven days later, the cow is given a second, breeding injection of prostaglandin. The cow is bred by appointment 72-80 hours after the breeding injection. Eighteen days later, the cow is tested for pregnancy using the compositions and methods of this invention.

Example 3

A cycling cow is given an injection of GnRH. Seven days later, the cow is given an injection of prostaglandin, such as 5 cc of LUTALYSE® Sterile Solution (Pharmacia, Peapack, N.J.). Two days later, a second injection of GnRH is given. The cow is bred by appointment 12-16 hours after the second GnRH injection. Eighteen days later, the cow is tested for pregnancy using the compositions and methods of this invention.

Example 4

A lactating dairy cow is presynchronized with a first injection of prostaglandin (25 mg of $PGF_{2\alpha}$ as LUTALYSE® Sterile Solution (Pharmacia, Peapack, N.J.) at 37 days postpartum and a second injection of prostaglandin at 51 days postpartum. The cow is synchronized with an injection of GnRH on day 63, an injection of prostaglandin on day 70, and a final injection of GnRH on day 72. On day 73, the cow is bred by timed artificial insemination. Eighteen days after breeding, the cow is tested for pregnancy using the compositions and methods of this invention.

Example 5

Eighty-two bred cows were tested for pregnancy using the compositions and methods of this invention. At Day 16, 17, 18, 19 or 20 following breeding, tail blood was drawn from each animal, and tested by ISG17 ELISA and/or dotblot (see Examples 22-24). These eighty-two cows were then tested for pregnancy using ultrasound at Day 30 and Day 50. A summary of the data is presented in Table 1 and the raw data is presented Table 2.

TABLE 1

|  | ISG17 | Ultrasound | Number |
| --- | --- | --- | --- |
| pregnant | + | + | 20 |
| not pregnant | − | − | 26 |
| false negative | − | + | 3 |
| spontaneous abortion or false positive | + | − | 24 |
| inconclusive | ? | ? | 9 |

Twenty cows were identified as pregnant by all tests. Twenty-six cows were identified as not pregnant by both tests. Nine cows tested inconclusively. Twenty-four cows were identified as pregnant by the compositions and methods of this invention, but not pregnant by ultrasound. These are labeled as false positive. The majority of these cows had spontaneous abortions after testing for the presence of ISG17. False positives are positive for ISG17 but negative for ultrasound. False negatives are negative for ISG17 and positive for ultrasound.

TABLE 2

| Cow ID | DSB* | Date Sampled | ELISA Ex. 23 | ELISA Ex. 22 | Dotblot Ex. 24 | Consensus | ultrasound Day 30 | Day 50 confirmation | Diagnosis | Status |
| --- | --- | --- | --- | --- | --- | --- | --- | --- | --- | --- |
| 877 | H | 18 | Dec. 02, 2001 | neg | nd | neg | neg | neg |  | correct | open |
| 997 | H | 17 | Dec. 02, 2001 | neg | nd | neg | neg | neg |  | correct | open |
| 1370 | H | 17 | Dec. 02, 2001 | pos | nd | pos | pos | pos |  | correct | bred |
| 1378 | H | 17 | Dec. 02, 2001 | neg | nd | pos |  | neg |  | nd |  |
| 1389 | H | 18 | Dec. 02, 2001 | neg | nd | pos |  | neg |  | nd |  |
| 1625 | H | 17 | Dec. 02, 2001 | pos/neg | nd | pos | pos | pos |  | correct | bred |
| 1674 | H | 18 | Dec. 02, 2001 | neg | nd | neg | neg | neg |  | correct | open |

TABLE 2-continued

| Cow ID | DSB* | | Date Sampled | | | | | | | Diagnosis | Status |
|---|---|---|---|---|---|---|---|---|---|---|---|
| 1681 | H | 17 | Dec. 02, 2001 | pos | nd | pos | pos | neg | | false pos | |
| 3152 | LL | 16 | Dec. 01, 2001 | nd | nd | neg | neg | neg | | correct | open |
| 3183 | LL | 16 | Dec. 01, 2001 | pos | nd | pos | pos | neg | | false pos | |
| 7006 | H | 17 | Dec. 02, 2001 | pos | nd | pos | pos | neg | | false pos | |
| 8017 | LL | 16 | Dec. 01, 2001 | neg | nd | neg | neg | neg | | correct | open |
| 8018 | LL | 16 | Dec. 01, 2001 | pos | nd | pos | pos | pos | | correct | bred |
| 8037 | LL | 16 | Dec. 01, 2001 | neg | nd | pos | | neg | | nd | |
| 8038 | LL | 16 | Dec. 01, 2001 | pos | nd | neg | | neg | | nd | |
| 8091 | LL | 16 | Dec. 01, 2001 | neg | nd | neg | neg | neg | | correct | open |
| 8092 | LL | 16 | Dec. 01, 2001 | nd | nd | neg | neg | neg | | correct | open |
| 8101 | LL | 16 | Dec. 01, 2001 | pos | nd | pos | pos | neg | | false pos | |

| Cow ID | DSB* | Date Sampled | ELISA Ex. 23 | ELISA Ex. 22 | Dotblot Ex. 24 | Consensus | ultrasound Day 30 | Day 50 confirmation | Diagnosis | Status |
|---|---|---|---|---|---|---|---|---|---|---|
| 2535 | 17 | Feb. 17, 2002 | neg | pos | pos | pos | neg | | false pos | |
| 2622 | 17 | Feb. 17, 2002 | pos | pos | pos | pos | neg | | false pos | |
| 2718 | 17 | Feb. 17, 2002 | pos | neg | pos | pos | pos | | correct | bred |
| 2723 | 17 | Feb. 17, 2002 | pos | pos | neg | pos | pos | | correct | bred |
| 2727 | 17 | Feb. 17, 2002 | pos | neg | neg | neg | neg | | correct | open |
| 2750 | 17 | Feb. 17, 2002 | neg | neg | neg | neg | neg | | correct | open |
| 2862 | 17 | Feb. 17, 2002 | neg | neg | neg | neg | pos | | false neg | |
| 2970 | 17 | Feb. 17, 2002 | neg | neg | neg | neg | neg | | correct | open |
| 8063 | 17 | Feb. 17, 2002 | neg | neg | neg | neg | neg | | correct | open |
| 8065 | 17 | Feb. 17, 2002 | pos | neg | pos | pos | neg | | false pos | |
| 8111 | 17 | Feb. 17, 2002 | pos | pos | pos | pos | neg | | false pos | |
| 8626 | 18 | Feb. 25, 2002 | neg | neg | neg | neg | neg | | correct | open |
| 8630 | 18 | Feb. 25, 2002 | pos | pos | pos | pos | neg | | false pos | |
| 8637 | 18 | Feb. 25, 2002 | neg | neg | neg | neg | neg | | correct | open |
| 8645 | 18 | Feb. 25, 2002 | pos | pos | pos | pos | pos | | correct | bred |
| 8647 | 18 | Feb. 25, 2002 | neg | pos | pos | pos | pos | | correct | bred |
| 8668 | 18 | Feb. 25, 2002 | pos | pos | pos | pos | neg | | false pos | |
| 8673 | 18 | Feb. 25, 2002 | pos | pos | pos | pos | pos | | correct | bred |
| 8711 | 18 | Feb. 25, 2002 | pos | pos | pos | pos | neg | | false pos | |
| 8752 | 18 | Feb. 25, 2002 | pos | pos | neg | pos | neg | | false pos | |
| 8762 | 18 | Feb. 25, 2002 | neg | nd | neg | neg | neg | | correct | open |
| 8764 | 18 | Feb. 25, 2002 | pos | pos | pos | pos | pos | | correct | bred |
| 8771 | 18 | Feb. 25, 2002 | pos | neg | pos | pos | pos | | correct | bred |
| 8779 | 18 | Feb. 25, 2002 | pos | pos | pos | pos | pos | | correct | bred |
| 8784 | 18 | Feb. 25, 2002 | pos | pos | pos | pos | neg | | false pos | |
| 8788 | 18 | Feb. 25, 2002 | neg | neg | neg | neg | neg | | correct | open |
| 8791 | 18 | Feb. 25, 2002 | neg | pos | pos | pos | pos | | correct | bred |
| 8793 | 18 | Feb. 25, 2002 | nd | pos | neg | | neg | | nd | |
| 577 | 20 | Mar. 13, 2002 | pos | pos | pos | pos | pos | | correct | bred |
| 826 | 18 | Mar. 13, 2002 | pos | pos | pos | pos | neg | | false pos | |
| 1050 | 18 | Mar. 13, 2002 | neg | pos | pos | pos | pos | | correct | bred |
| 2467 | 17 | Mar. 13, 2002 | neg | neg | neg | neg | neg | | correct | open |
| 2578 | 17 | Mar. 13, 2002 | neg | pos | pos | pos | neg | | false pos | |
| 2818 | 17 | Mar. 13, 2002 | pos/neg | pos | pos | pos | neg | | false pos | |
| 3309 | 18 | Mar. 13, 2002 | nd | pos | pos | pos | neg | | false pos | |
| 3768 | 20 | Mar. 13, 2002 | pos | pos | pos | pos | pos | | correct | bred |
| 6555 | 18 | Mar. 13, 2002 | nd | pos | neg | | neg | | nd | |
| 7288 | 17 | Mar. 13, 2002 | nd | pos | neg | | pos | | nd | |
| 8699 | 19 | Mar. 13, 2002 | pos | pos | pos | pos | pos | | correct | bred |
| 9494 | 17 | Mar. 13, 2002 | neg | pos | pos | pos | neg | | false pos | |
| 11703 | 18 | Mar. 13, 2002 | pos | pos | pos | pos | neg | | false pos | |
| 12885 | 19 | Mar. 13, 2002 | pos | pos | pos | pos | neg | | false pos | |
| 12915 | 20 | Mar. 13, 2002 | pos | pos | pos | pos | pos | | correct | bred |
| 12930 | 19 | Mar. 13, 2002 | pos | pos | neg | pos | neg | | false pos | |
| 13514 | 18 | Mar. 13, 2002 | neg | pos | pos | pos | pos | | correct | bred |
| 13528 | 19 | Mar. 13, 2002 | pos/neg | pos | neg | | neg | | nd | |
| 13541 | 17 | Mar. 13, 2002 | pos | pos | pos | pos | pos | | correct | bred |
| 13619 | 20 | Mar. 13, 2002 | pos/neg | neg | neg | neg | neg | | correct | open |
| 13622 | 19 | Mar. 13, 2002 | neg | neg | pos | neg | neg | | correct | open |
| 13736 | 18 | Mar. 13, 2002 | pos | pos | pos | pos | neg | | false pos | |
| 13756 | 19 | Mar. 13, 2002 | pos | neg | pos | pos | neg | | false pos | |
| 13759 | 20 | Mar. 13, 2002 | pos | neg | neg | neg | pos | neg | correct | open |
| 14147 | 20 | Mar. 13, 2002 | neg | neg | neg | neg | neg | | correct | open |
| 14645 | 17 | Mar. 13, 2002 | pos/neg | neg | pos | | neg | | nd | |
| 14654 | 17 | Mar. 13, 2002 | neg | neg | pos | neg | pos | pos | false neg | |
| 14767 | 17 | Mar. 13, 2002 | neg | neg | neg | neg | neg | neg | correct | open |
| 7010 | 19 | Mar. 18, 2002 | pos | pos | pos | pos | pos | | correct | bred |
| 12830 | 18 | Mar. 18, 2002 | nd | neg | neg | neg | pos | pos | false neg | |
| 12896 | 18 | Mar. 18, 2002 | nd | neg | nd | neg | neg | | correct | open |
| 12971 | 18 | Mar. 18, 2002 | nd | pos | pos | pos | neg | | false pos | |
| 13525 | 19 | Mar. 18, 2002 | neg | neg | pos | neg | neg | neg | correct | open |
| 13587 | 18 | Mar. 18, 2002 | neg | neg | neg | neg | neg | | correct | open |
| 13633 | 18 | Mar. 18, 2002 | neg | neg | nd | neg | pos | neg | correct | open |
| 14666 | 19 | Mar. 18, 2002 | neg | neg | nd | neg | neg | | correct | open |

TABLE 2-continued

| | | |
|---|---|---|
| 3200 | 17 | Apr. 21, 2002 |
| 3235 | 17 | Apr. 21, 2002 |
| 3237 | 17 | Apr. 21, 2002 |
| 3247 | 17 | Apr. 21, 2002 |
| 3249 | 17 | Apr. 21, 2002 |
| 3253 | 17 | Apr. 21, 2002 |
| 3262 | 17 | Apr. 21, 2002 |
| 3275 | 17 | Apr. 21, 2002 |
| 8090 | 17 | Apr. 21, 2002 |
| 8114 | 17 | Apr. 21, 2002 |
| 8122 | 17 | Apr. 21, 2002 |
| 8123 | 17 | Apr. 21, 2002 |
| 8127 | 17 | Apr. 21, 2002 |
| 8129 | 17 | Apr. 21, 2002 |
| 8130 | 17 | Apr. 21, 2002 |
| 8131 | 17 | Apr. 21, 2002 |
| 8132 | 17 | Apr. 21, 2002 |
| 8145 | 17 | Apr. 21, 2002 |
| 8159 | 17 | Apr. 21, 2002 |
| 8171 | 17 | Apr. 21, 2002 |
| 8178 | 17 | Apr. 21, 2002 |
| 8183 | 17 | Apr. 21, 2002 |
| 8186 | 17 | Apr. 21, 2002 |

*DSB = days since last bred

In Table 2, the ELISAs utilized 5E9 as the colloidal gold-labeled detection antibody and anti-ISG17-1000 as the capture antibody. The dotblot utilized anti-ISG17-4245. A hybridoma that produces antibody 5E9 has been deposited with the American Type Culture Collection under the Budapest Treaty on the International Recognition of The Deposit of Microorganisms for the Purposes of Patent Procedure under deposit number PTA-7960.

Example 6

A bred cow is tested for pregnancy using the compositions and methods of this invention eighteen days following breeding. The cow is determined to be non pregnant. The cow is observed for behavioral estrus. Behavioral estrus is observed, and the cow is bred. Eighteen days later the twice-bred cow is tested for pregnancy using the compositions and methods of this invention. The cow is determined to be pregnant.

Example 7

A bred cow is tested for pregnancy using the compositions and methods of this invention eighteen days following breeding. The cow is determined to be non-pregnant. The cow is given a prostaglandin injection. 72-80 hours later the cow is bred. Eighteen days later the twice-bred cow is tested for pregnancy using the compositions and methods of this invention. The cow is determined to be pregnant.

Example 8

100 bred cows were tested for pregnancy using the compositions and methods of this invention eighteen days following breeding and determined to be non-pregnant. Each of the 100 cows is given a prostaglandin injection. 72-80 hours following the injection, each cow is bred. Eighteen days later, each twice-bred cow is tested for pregnancy using the compositions and methods of this invention.

Example 9

Antigenicity plotting was performed on the translated sequence of ISG17. Four regions of high antigenicity were identified. Region 1 corresponded to amino acids 43-56 (SEQ ID NO: 1). Region 2 corresponded to amino acids 82-100. Region 3 corresponded to amino acids 100-115 (SEQ ID NO: 3). Region 4 corresponded to amino acids 120-135 (SEQ ID NO: 5). The sequence of each region was compared to the sequences of ubiquitin and all other known UCRPs (bovine, ovine, mouse, and human). Region 4 showed high homology with ubiquitin. Region 2 was used by Pru (Pru, J. K. (2000) "Appendix 1: Production of Recombinant Bovine Interferon Stimulated Gene Product 17 Antibodies" Ph.D. Thesis, University of Wyoming) to generate polyclonal antibodies, but these were unable to recognize native ISG17 protein. Region 1 was chosen for making antibodies.

Example 10

The amino acid sequence CQRLAHLDSREVLQE (SEQ ID NO: 2) was submitted to Bethyl Laboratories, Inc (Montgomery, Tex.) for the production of polyclonal antibodies. The corresponding polypeptide was synthesized, purified by HPLC, and verified by mass spectrometry. Polyclonal antibodies, anti-ISG17-4245, were produced in rabbits by injecting the purified polypeptide linked to a keyhole limpet hemocyanin (KLH) carrier using maleimide chemistry. Anti-ISG17-4245 was affinity purified by linking the KLH linked polypeptide to agarose using a cyanogen bromide method for capture, and a portion of the purified antibody was conjugated to horseradish peroxidase (HRP) using a periodate method. Antibodies were treated to remove antibodies that aggregated when denatured.

Example 11

The polypeptide corresponding to amino acid sequence CQRLAHLDSREVLQE (SEQ ID NO: 2) is synthesized. Monoclonal antibodies and corresponding hybridoma cell lines are produced to this polypeptide by administering said peptide to a mammal under conditions appropriate for stimulation of an immune response, isolating antibody producing cells from the mammal, fusing the antibody producing cells, with immortalizing cells to produce a hybridoma cell line, and screening the resulting hybridoma cell lines to identify a cell line secreting antibody having the desired specificity.

Example 12

Recombinant bovine ISG17 (rboISG17) was made in *E. coli* using a pGEX4T-1 plasmid with the bovine cDNA inserted downstream of GST. The resulting GST-ISG17 was purified using standard glutathione-5-transferase (GST) chromatography followed by cleavage of ISG17 from GST. The *E. coli* host is BL21. The purified protein was submitted to Bethyl Laboratories, Inc (Montgomery, Tex.) for the production of polyclonal antibodies to make anti-ISG17-1000 in rabbits. Anti-ISG17-1000 was affinity purified by linking rboISG17 to agarose using a cyanogen bromide method for capture, and a portion of the purified antibody was conjugated to horseradish peroxidase (HRP) using a periodate method. Antibodies were treated to remove antibodies that aggregated when denatured.

Example 13

Hybridoma cells producing monoclonal antibody 5E9 were obtained from T. R. Hansen, University of Wyoming. 5E9 hybridoma cells were cultured, and 5E9 antibody was purified with T-gel (Pierce, Rockford, Ill.).

Example 14

Polyclonal antibodies anti-ISG17-4245 and anti-ISG17-1000, and monoclonal antibody 5E9 were characterized. Both polyclonal antibodies were able to bind native bovine ISG17. Anti-ISG17-4245 was also able to bind ovine ISG17. Neither was able to bind substantially to ubiquitin. The binding site of the 5E9 antibodies was characterized by dot blot and ELISA. ELISA demonstrated that 5E9 recognizes bovine and ovine ISG17 and that 5E9 binds to ISG17 while anti-ISG17-1000 or while anti-ISG17-4245 is simultaneously bound. Dot blots demonstrated that 5E9 does not bind to polypeptides CQRLAHLDSREVLQE (SEQ ID NO:2) (the epitope recognized by anti-ISG17-4245), TVAELKQQVC-QKERVQ (SEQ ID NO:3), or the polypeptide sequence of amino acids 82-99 of ISG17.

Example 15

A 1:1000 dilution of polyclonal antibody anti-ISG17-4245 was bound to a 96 well plate. A serial dilution of recombinant ISG17 was added to the plate and allowed to incubate for one hour then washed. A 1:1000 dilution of 5E9 monoclonal antibody was added to the plate and allowed to incubate for one hour then washed. The 5E9 antibody was not conjugated to an enzyme, therefore a 1:000 dilution of horseradish peroxidase (HRP) conjugated anti mouse antibody was added to the plate and allowed to incubate for one hour then washed. Tetramethyl benzidine (TMB) (3,3'-5,5'-tetramethylbenzidine, DAKO USA) substrate was added to the plate and allowed to incubate until a sufficient blue color appeared, then a stop reagent was added to produce a yellow color which was then read at 450 nm. The absorbance readings for this ELISA were as follows:

TABLE 3

| ISG 17 (µg/ml) | Absorbance |
|---|---|
| 0 | 0.0108 |
| 1 | 0.0109 |
| 10 | 0.0240 |
| 25 | 0.2220 |
| 50 | 0.1096 |
| 100 | 0.3807 |

This experiment demonstrated that ISG17 was being captured by polyclonal antibody ISG-4245 and detected by monoclonal antibody 5E9. 5E9 is shown to recognize a specific region that is found in more then one place within the molecule. If 5E9 only detected the region that anti-ISG17-4245 was bound to in this ELISA, a curve would not have been obtained.

Example 16

Blood samples were obtained from bred cows eighteen days after breeding. The serum was tested for the presence of ISG17 using antibodies anti-ISG17-4245, anti-ISG17-1000, and 5E9. The cows were monitored for pregnancy/non pregnancy with ultrasound. The presence of ISG17 on day eighteen correlated with pregnancy.

Example 17

An immunoassay test device, for testing for pregnancy by detection of ISG17, was made. The device contains 5E9 labeled with gold as the detection antibody and anti-ISG17-1000 as the capture antibody. Similar devices are made containing one or more antibodies chosen from anti-ISG17-4245, anti-ISG17-1000, and 5E9.

Example 18

An immunoassay test device is used to test a cow for pregnancy. Whole blood is drawn from the tail vein on Day eighteen following breeding. The blood is placed on the sample window and five minutes are allowed to pass. A dark line appears in the test area and a dark line appears in the control area. The cow is determined to be pregnant.

Example 19

An immunoassay test device is used to test a cow for pregnancy. Whole blood is drawn from the tail vein on Day eighteen following breeding. The blood is placed in the sample window and five minutes pass. A dark line appears the control area. No dark line appears in the test area. The cow is determined to be not pregnant.

Example 20

An immunoassay test device was used to test cows for pregnancy. Whole blood was drawn on day eighteen following breeding. Whole blood was applied inside the sample window of the device. Plasma was separated from serum in the device. The plasma tested positive for ISG17 and flow control indicating the cows were pregnant.

Example 21

An immunoassay test device is used to test cows for pregnancy. Whole blood is drawn on day eighteen following breeding. Serum is separated from the whole blood. The serum is applied in the sample window of the device. The serum tests positive for ISG17 and flow control indicating the cows were pregnant.

Example 22

ISG17 levels are measured in cows after spontaneous abortion. After artificial insemination, blood is drawn on each of Days 1-30, from each of ten cows. The blood samples are tested for the presence of ISG17, by lateral flow immunoassay and Western blot. The lateral flow immunoassay utilizes anti-ISG17-1000 as the capture antibody and 5E9 labeled with colloidal gold as the detection antibody. At Day 30 the cows are tested by ultrasound.

Example 23

ISG17 ELISA #1 was performed as follows: The plate was coated with 100 μl of a 1:1000 dilution of anti-ISG17-1000 polyclonal antibody diluted in phosphate-buffered saline (PBS) and allowed to bind to the plate for approximately 1 hour. The antibody was dumped off and 250 μl of 1× Uniblock (Analytical Genetic Testing Center, Inc., Denver, Colo.) was added and allowed to block for approximately 1 hour. The Uniblock was removed and the antigen sample added. A serial dilution of ISG17 was added to the plate to obtain a standard curve. 1 ug/ml, 10 ug/ml, 25 ug/ml, 50 ug/ml, 75 ug/ml, and 100 ug/ml diluted in PBS were used. 100 μl of each dilution was added to the plate. For the serum samples, 50 μl of plasma and 50 μl of PBS were added to the wells. The sample was incubated for approximately 1 hour. The plate was washed three times with 250 μl of PBS and dried. 100 μl of a 1:100 dilution of horseradish peroxidase (HRP)-conjugated anti-4245peptide polyclonal antibody diluted in 1× Uniblock was added to each well and allowed to incubate for approximately 1 hour. The plate was washed five times with 250 μl PBS and dried. 100 μl of 3,3',5,5'-tetrazinethylbenzidine (TMB) was added to each well. Sufficient color change was allowed to occur, and then 50 μl of acid stop was added. The plate was read at 450 nm.

Example 24

ISG17 ELISA #2 was performed as follows: 100 μl of diluted primary antibody was added to each well of a microtiter plate. The plate was covered and incubated overnight at 4° C. Liquid was removed. 150 μl non-specific binding (NSB) bovine serum albumin-phosphate-buffered saline (1.0% BSA-PBS) was added to each well, and the plates were covered and incubated for 1 hour at 37° C. The plate was washed three times with PBST (0.1 M sodium phosphate, 0.15 M sodium chloride, pH 7.2, 0.01 Tween 20) using an automatic plate washer. 50 μl of diluted standard or unknown sample plasma was added to each well. The plate was covered and incubated for 1 hour at room temperature on a rotator. The plate was washed three times with PBST using an automatic plate washer. 100 μl of labeled antibody was added to each well. The plate was covered and incubated at room temperature (RT) for 1 hour on a rotator. The plate was washed three times using an automatic plate washer and tapped on adsorbent towels to thoroughly dry the wells. 100 μl of Dako TMB reagent was added. Plates were incubated for 10-15 minutes at RT. Reactions were stopped by adding 100 μl 1N $H_2SO_4$. Absorbance was read at 450 nm.

Example 25

ISG17 dotblot was performed as follows: Nitrocellulose paper was dotted with ISG17 dilutions. 100 ng (1 μl of 100 ug/ml dilution in PBS), 50 ng, 20 ng, 10 ng, and 2 ng were used. A dot of 2 mg/ml BSA was used as a negative control. 5 μl of each plasma sample was dotted on the membrane and allowed to dry. The membrane was blocked in 1× Uniblock for 1 hour. A 1:500 dilution of HRP conjugated polyclonal antibody anti-ISG17-4245 diluted in 1× Uniblock was added and incubated for 1 hour. The membrane was washed at least three times for 10 minutes, each wash in PBS. A detection substrate, SuperSignal from Pierce (Rockford, Ill.), was added and detected on film. The 1:500 dilution of the antibody gave a very strong signal.

Example 26

Test strips were made using anti-ISG17-1000 as a first capture antibody, anti-ISG17-4245 labeled with colloidal gold as a second detection antibody, and anti-rabbit antibodies as flow control capture antibodies. Blood from 20 cows between day 18 and 20 after AI was drawn. The blood was centrifuged at the dairy, transported to the lab, and tested using devices containing the above-described test strips. 20 ul of plasma from each cow, followed by 60 ul of chase buffer, was added to each cassette and read after 5-10 minutes. Ultrasound was performed at day 26-28 for confirmation. The results are shown in Table 4.

TABLE 4

| Cow | Days AI | Control value | Test line value | Result (based on value) | Result (based on visual) | ULT |
|---|---|---|---|---|---|---|
| 1 | 18 | 1656 | 89 | wpos | pos | preg |
| 2 | 19 | 1752 | 447 | pos | strong pos | o |
| 3 | 18 | 1688 | 99 | wpos | pos | o |
| 4 | 19 | 1832 | 273 | pos | pos | o |
| 5 | 19 | 1726 | 154 | pos | pos | o |
| 6 | 19 | 1652 | 122 | pos | pos | preg |
| 7 | 19 | 1672 | 168 | pos | pos | o |
| 8 | 19 | 1716 | 210 | pos | pos | o |
| 9 | 19 | 1742 | 764 | pos | pos | preg |
| 10 | 19 | 1737 | 30 | neg | neg | o |
| 11 | 19 | 1739 | 65 | wpos | vwpos | o |
| 12 | 19 | 1673 | 31 | neg | neg | o |
| 13 | 19 | 1743 | 45 | neg | neg | o |
| 14 | 19 | 1959 | 89 | wpos | vwpos | o |
| 15 | 20 | 1752 | 157 | pos | wpos | o |
| 16 | 19 | 1701 | 245 | pos | pos | o |
| 17 | 19 | 1651 | 418 | pos | pos | preg |

TABLE 4-continued

| Cow | Days AI | Control value | Test line value | Result (based on value) | Result (based on visual) | ULT |
|---|---|---|---|---|---|---|
| 18 | 19 | 1643 | 60 | wpos | wpos | preg |
| 19 | 19 | 1721 | 99 | wpos | wpos | preg |
| 20 | 19 | 1735 | 26 | neg | neg | o |

The intensity of the test and control lines can be quantitated using methods known in the art. The intensities of the control line and test line were quantitated by converting a scan of each device into pixels using software Cut off values are useful for determining objective methods for reading negative and weakly positive results. As confirmed by ultrasound, six cows were correctly identified as pregnant and four cows were correctly identified as not pregnant using the methods and compositions of this invention. Ten cows that were determined to be pregnant at Day 18 or 19 were determined by ultrasound to not be pregnant at Day 26. No cows that were determined to be not pregnant were later determined by ultrasound to be pregnant.

One liter of chase buffer contains 2.13 gm/L of sodium phosphate dibasic, 8.77 gm/L sodium chloride, 5 mg/L polyvinylpyrrolidone (PVP, molecular weight=10,000), 1 gm/L sodium azide, and the balance is deionized water. The pH is brought to 7.4 using HCl.

Example 27

Test strips were made using anti-ISG17-1000 as a first capture antibody, anti-ISG17-4245 labeled with colloidal gold as a second detection antibody, and anti-rabbit antibodies as flow control capture antibodies. 81 cows on days 18-20 were drawn at a dairy and the blood samples transported to a lab where they were centrifuged and assayed using devices containing the above-described test strips. 20 ul of plasma was added to the cassette followed by 60 ul of chase buffer. The test was read after about 5 to 10 minutes. Tests were read as positive (+), faint positive (+f), very faint positive (+vf) or negative (−). Positive, faint positive, and very faint positive were scored as pregnant. The cows were checked for pregnancy by ultrasound on Day 26 and again at Day 50 by palpation. The results are shown in Table 5.

TABLE 5

| Sample | Cassette Result | 26 day Ultrasound | 50 day Palpation |
|---|---|---|---|
| 1 | + | | |
| 2 | + | | |
| 3 | − | | |
| 4 | − | | |
| 5 | + | | |
| 6 | + f | | |
| 7 | + f | + | + |
| 8 | + f | | |
| 9 | + | + | + |
| 10 | + f | + | |
| 11 | − | | |
| 12 | − | | |
| 13 | + f | | |
| 14 | − | | |
| 15 | − | | |
| 16 | − | | |
| 17 | − | | |
| 18 | − | | |
| 19 | + | + | + |
| 20 | + f | + | |
| 21 | − | | |
| 22 | + vf | | |
| 23 | − | | |
| 24 | − | | |
| 25 | + | | |
| 26 | − | | |
| 27 | + vf | + | + |
| 28 | + vf | | |
| 29 | + vf | + | |
| 30 | + | + | |
| 31 | + vf | | |
| 32 | + vf | | |
| 33 | + f | | |
| 34 | + | | |
| 35 | + f | | |
| 36 | − | | |
| 37 | − | | |
| 38 | + f | | |
| 39 | + f | | |
| 40 | + vf | | |
| 41 | − | + | + |
| 42 | − | | |
| 43 | + | | |
| 44 | − | | |
| 45 | − | | |
| 46 | − | | |
| 47 | − | | |
| 48 | + vf | | |
| 49 | − | | |
| 50 | − | | |
| 51 | + | | |
| 52 | + vf | + | + |
| 53 | + vf | + | |
| 54 | + vf | | |
| 55 | − | | |
| 56 | + vf | | |
| 57 | − | | |
| 58 | + f | + | + |
| 59 | + | | |
| 60 | − | | |
| 61 | − | | |
| 62 | − | | |
| 63 | − | | |
| 64 | − | | |
| 65 | + f | + | + |
| 66 | + f | | |
| 67 | + | | |
| 68 | + | | |
| 69 | + f | + | + |
| 70 | + f | | |
| 71 | − | | |
| 72 | + | | |
| 73 | + f | | |
| 74 | + f | | |
| 75 | − | | |
| 76 | − | | |
| 77 | − | | |
| 78 | − | | |
| 79 | + f | + | + |
| 80 | + | | |
| 81 | − | | |

Of the 81 samples tested, there were 15 positive and 66 negative scores by ultrasound. Of the 15 positive, 14 were determined to be pregnant using the compositions and methods of this invention. Of the 66 negative, 34 were determined to be non-pregnant and 32 were determined to be pregnant between Days 18-20 using the compositions and methods of this invention.

It will be appreciated by those of ordinary skill in the art that hormones, methods for forcing estrus, antibodies, devices, immunoassays, expression assays, detection methods, methods of making antibodies, and hormones other than those specifically disclosed herein are available in the art and can be employed in the practice of this invention. All art-known functional equivalents are intended to be encompassed within the scope of this invention.

All references cited in the present application are incorporated by reference herein to the extent that there is no inconsistency with the present disclosure.

We claim:

1. A method of detecting pregnancy in a female sheep or cow comprising detecting interferon-stimulated gene 17 (ISG17) in a test sample of blood or serum from a female sheep or cow, said method comprising:
   (a) providing an immunoassay test device comprising:
      i. at least one absorbent support;
      ii. an antibody specific to said ISG17 on a said absorbent support;
      iii a flow control component on a said absorbent support;
      iv. means for detecting binding of said antibody with said ISG17; and
      v. means for comparing the binding level of ISG17 in the test sample with a background binding level of ISG17 in a control sample from a non-pregnant animal of the same species;
   (b) flowing the sample into the immunoassay test device into contact with the antibody;
   (c) detecting a binding level of said antibody with said ISG17 in the test sample greater than that of the binding level of said antibody with ISG17 in a control sample from a non-pregnant animal of the same species, said greater binding level of said antibody with ISG17 in the test sample being indicative of pregnancy; and
      wherein said method does not comprise a cell-lysing step.

2. The method of claim 1 comprising collecting said sample from said sheep or cow and detecting said binding outside a laboratory.

3. The method of claim 1 wherein said test sample is obtained on a day selected from the group consisting of Day 11, Day 32, and intervening days after breeding.

4. The method of claim 3 wherein said breeding comprises performing artificial insemination.

5. The method of claim 3 wherein said breeding is preceded by forced estrus.

6. The method of claim 1 wherein said test sample is obtained on a day selected from the group consisting of Day 15, Day 25, and intervening days after breeding.

7. The method of claim 1 wherein said test sample is obtained on a day selected from the group consisting of Day 18, Day 22, and intervening days after breeding.

8. The method of claim 1 wherein said sample is obtained on a day selected from Day 18 or Day 19 after breeding.

9. The method of claim 1 wherein said test sample is obtained on Day 18 after breeding.

10. The method of claim 1 wherein said test sample is obtained on Day 19 after breeding.

11. The method of claim 1 wherein said sheep or cow is not infected with a virus.

12. The method of claim 1 wherein said test sample is blood.

13. The method of claim 12 also comprising filtering the blood sample to obtain serum containing said ISG17.

14. The method of claim 1 performed outside a laboratory.

15. The method of claim 1 wherein said antibody is selected from the group consisting of: monoclonal and polyclonal antibodies generated with and capable of specific binding to an amino acid sequence selected from the group consisting of QRLAHLDSREVLQE (SEQ ID NO: 1), CQRLAHLDSREVLQE (SEQ ID NO: 2), TVAELKQQVCQKERVQ (SEQ ID NO: 3), CTVAELKQQVCQKERVQ (SEQ ID NO: 4), WLSFEGRPMDDEHPLE (SEQ ID NO: 5), and CWLSFEGRPMDDEHPLE (SEQ ID NO: 6); and monoclonal and polyclonal antibodies generated with other complete or partial amino acid sequences from mammalian ISG17.

16. The method of claim 1 comprising comparing binding of said antibody with ISG17 in said test sample with binding of said antibody in a second control sample containing normal background levels of said ISG17.

17. The method of claim 16 also comprising binding a second antibody to said ISG17 in said test sample.

18. The method of claim 1 wherein said antibody specific to ISG17 is 5E9, wherein a hybridoma that produces said antibody is deposited as ATCC Deposit No. PTA-7960.

19. The method of claim 1 also comprising binding a second antibody to ISG17 to said ISG17 in said test sample.

20. The method of claim 19 wherein said antibody and said second antibody bind to substantially distinct epitopes.

21. A method of breeding of a female sheep or cow comprising:
   (1) detecting non-pregnancy in the sheep or cow by a method comprising:
      (a) on a day that is after a first breeding of said sheep or cow, wherein said sheep or cow was bred during estrus, said day being before estrus of said sheep or cow is next expected, obtaining a sample of blood or serum from said sheep or cow;

(b) providing an immunoassay device comprising:
  i. at least one absorbent support;
  ii. an antibody specific to said ISG17 on a said absorbent support;
  iii a flow control component on a said absorbent support;
  iv. means for detecting binding of said antibody with said ISG17; and
  v. means for comparing the binding level of ISG17 in the test sample with a background binding level of ISG17 in a control sample from a non-pregnant animal, a pregnant animal or a recently-aborted animal of the same species;
(c) flowing the sample into the immunoassay test device into contact with the antibody;
(d) detecting a binding level of said antibody with said ISG17 in the test sample not greater than that of said binding level with ISG17 in a control sample from a non-pregnant animal or recently-aborted animal of the same species, or less than that of said binding level of ISG17 in a control sample from a pregnant animal of the same species;
  said binding level of said antibody with ISG17 in the test sample not greater than that in the control sample from a non-pregnant animal or recently-aborted animal of the same species, or said binding level with ISG17 in the test sample less than that in the control sample from a pregnant animal of the same species being indicative of non-pregnancy;
  wherein said method does not include a cell-lysing step;
(2) if the sheep or cow is determined not to be pregnant, forcing estrus or monitoring for and detecting signs of behavioral estrus; and
(3) effecting a second breeding of said sheep or cow.

22. A method detecting non-pregnancy in a sheep or cow by a method comprising:
  (1) obtaining a sample of blood or serum from said sheep or cow;
  (2) providing an immunoassay device comprising:
    (a) at least one absorbent support;
    (b) an antibody specific to said ISG17 on a said absorbent support;
    (c) a flow control component on a said absorbent support;
    (d) means for detecting binding of said antibody with said ISG17; and
    (e) means for comparing the binding level of ISG17 in the test sample with a background binding level of ISG17 in a control sample from a non-pregnant animal, a pregnant animal or a recently-aborted animal of the same species;
  (3) flowing the sample into the immunoassay test device into contact with the antibody;
  (4) detecting a binding level of said antibody with said ISG17 in the test sample not greater than that of said binding level with ISG17 in a control sample from a non-pregnant animal or recently-aborted animal of the same species, or less than that of said binding level of ISG17 in a control sample from a pregnant animal of the same species; said binding level of said antibody with ISG17 in the test sample not greater than that in the control sample from a non-pregnant animal or recently-aborted animal of the same species, or said binding level with ISG17 in the test sample less than that in the control sample from a pregnant animal of the same species being indicative of non-pregnancy;
  wherein said method does not include a cell-lysing step.

* * * * *